(12) United States Patent
Kitamura et al.

(10) Patent No.: US 7,655,834 B2
(45) Date of Patent: Feb. 2, 2010

(54) PLANT PIGMENT ACCUMULATION GENE

(75) Inventors: Satoshi Kitamura, Takasaki (JP);
Naoya Shikazono, Takasaki (JP);
Atsushi Tanaka, Takasaki (JP)

(73) Assignee: Japan Atomic Energy Research Institute, Kashiwa (JP)

( * ) Notice: Subject to any disclaimer, the term of this patent is extended or adjusted under 35 U.S.C. 154(b) by 327 days.

(21) Appl. No.: 10/797,035

(22) Filed: Mar. 11, 2004

(65) Prior Publication Data

US 2004/0181826 A1 Sep. 16, 2004

(30) Foreign Application Priority Data

Mar. 12, 2003 (JP) ............................. 2003-066310

(51) Int. Cl.
*C12N 15/29* (2006.01)
*C12N 15/52* (2006.01)
*C12N 15/82* (2006.01)
*A01H 5/00* (2006.01)

(52) U.S. Cl. ................... 800/282; 800/298; 435/419; 435/465

(58) Field of Classification Search ............... 536/23.1, 536/23.2, 23.6; 800/282, 298
See application file for complete search history.

(56) References Cited

FOREIGN PATENT DOCUMENTS

WO WO 02/10210 2/2002

OTHER PUBLICATIONS

Wagner U. et al. Plant Molecular Biology, Jul. 2002 ; vol. 49, pp. 515-532.*
Alfenito M. et al. The Plant Cell Jul. 1999; vol. 10, pp. 1135-1149.*
M. Alfenito, et al., "Functional Complementation of Anthocyanin Sequestration in the Vacuole by Widely Divergent Glutathione S-Transferases", The Plant Cell, vol. 10, 1135-1149, Jul. 1998, pp. 1135-1149.
L. Mueller, et al., "AN9, a Petunia Glutathione S-Transferase Required for Anthocyanin Sequestration, Is a Flavonoid-Binding Protein", Plant Physiology, vol. 123, Aug. 2000, pp. 1561-1570.
"Structural Analysis of *Arabidopsis thaliana* Chromosome 5. I. Sequence Features of the 1.6 b Regions Covered by Twenty Physically Assigned P1 Clones", Sato et al., DNA Research, vol. 4, pp. 215-230, Jun. 30, 1997.
GenBank Acc. No. Q96324, Alfenito et al., first published Jan. 15, 2001 (9 pp).

* cited by examiner

*Primary Examiner*—Russell Kallis
(74) *Attorney, Agent, or Firm*—Staas & Halsey LLP

(57) ABSTRACT

By analyzing the causative gene of tt19 mutants and elucidating the nature of the mutants, the present inventors found a novel gene as the causative gene and gave it the name TRANSPARENT TESTA (TT19) gene. The inventors cloned this gene and analyzed its DNA nucleotide sequence as well as the protein encoded by its DNA. The inventors also provided a transformed plant utilizing the nature of the identified causative gene.

8 Claims, 10 Drawing Sheets
(5 of 10 Drawing Sheet(s) Filed in Color)

SEQUENCE LISTING

<160> NUMBER OF SEQ ID NOS: 46

<210> SEQ ID NO 1
<211> LENGTH: 645
<212> TYPE: DNA
<213> ORGANISM: Arabidopsis thaliana

<400> SEQUENCE: 1
atggttgtga aactatatgg acaggtaaca gcagcttgtc cacaaagagt cttgctttgt    60

```
tttctcgaga aaggaattga atttgagatt attcatatcg atcttgatac atttgagcaa    120
aaaaaaccag aacatcttct tcgtcagcca tttggtcaag ttccagccat agaagatgga    180
gatttcaagc tttttgaatc acgagccatc gcgagatact acgctaccaa gttcgcggac    240
caaggcacga acctttgggg caagtctcta gagcaccgag ccatcgtgga ccagtgggct    300
gacgtggaga cctattactt caacgttctg gcccaacccc tcgtgattaa cctaatcatc    360
aagcctaggt taggcgagaa atgtgacgtc gttttggtcg aggatctcaa agtgaagcta    420
ggagtggtct tggacatata caataaccgg cttcttcga accggttttt ggctggtgaa    480
gaattcacta tggctgattt gacgcacatg ccggcgatgg ggtacttgat gagtataacc    540
gatataaacc agatggttaa ggctcggggt agtttaacc ggtggtggga agagatttcg    600
gatagaccgt cttggaagaa gcttatggtg ctggctggtc actga                   645
```

<210> SEQ ID NO 2
<211> LENGTH: 214
<212> TYPE: PRT
<213> ORGANISM: Arabidopsis thaliana

<400> SEQUENCE: 2

```
Met Val Val Lys Leu Tyr Gly Gln Val Thr Ala Ala Cys Pro Gln Arg
1               5                   10                  15

Val Leu Leu Cys Phe Leu Glu Lys Gly Ile Glu Phe Glu Ile Ile His
                20                  25                  30

Ile Asp Leu Asp Thr Phe Glu Gln Lys Pro Glu His Leu Leu Arg
            35                  40                  45

Gln Pro Phe Gly Gln Val Pro Ala Ile Glu Asp Gly Asp Phe Lys Leu
    50                  55                  60

Phe Glu Ser Arg Ala Ile Ala Arg Tyr Tyr Ala Thr Lys Phe Ala Asp
65                  70                  75                  80

Gln Gly Thr Asn Leu Leu Gly Lys Ser Leu Glu His Arg Ala Ile Val
                85                  90                  95

Asp Gln Trp Ala Asp Val Glu Thr Tyr Tyr Phe Asn Val Leu Ala Gln
            100                 105                 110

Pro Leu Val Ile Asn Leu Ile Ile Lys Pro Arg Leu Gly Glu Lys Cys
        115                 120                 125

Asp Val Val Leu Val Glu Asp Leu Lys Val Lys Leu Gly Val Val Leu
130                 135                 140

Asp Ile Tyr Asn Asn Arg Leu Ser Ser Asn Arg Phe Leu Ala Gly Glu
145                 150                 155                 160

Glu Phe Thr Met Ala Asp Leu Thr His Met Pro Ala Met Gly Tyr Leu
                165                 170                 175

Met Ser Ile Thr Asp Ile Asn Gln Met Val Lys Ala Arg Gly Ser Phe
            180                 185                 190

Asn Arg Trp Trp Glu Glu Ile Ser Asp Arg Pro Ser Trp Lys Lys Leu
        195                 200                 205

Met Val Leu Ala Gly His
    210
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3 gagaaccccca aaaacgtcac                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gttgtgaggg ttgggtagaa                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtggttgttg ggaagagaag                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgatggctcg tgattcttag                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtcaagttc cagccataga                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcgagagga aagtggaaca                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 9
ccctcattag gccaagagaa                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagcttatgt ggggaaagtc                                               20

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atcaagtacc ccatcgccgg catgt                                         25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcatgtgcg tcaaatcagc catag                                         25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaccggttcg aagaaagccg gttat                                         25

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atatggacag gtaacagcag cttgtc                                        26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
```

```
gcagcttgtc cacaaagagt cttgct                                          26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gctttgtttt ctcgagaaag gaattg                                          26

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gacgtcacat ttctcgccta acct                                            24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaggggttgg gccagaacgt tgaa                                            24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgatggctcg gtgctctaga gact                                            24

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: a, c, g or t
<220> FEATURE:
<221> NAME/KEY: modified_base
<222> LOCATION: (11)..(11)
<223> OTHER INFORMATION: a, c, g or t

<400> SEQUENCE: 20
ngtcgaswga nawgaa                                                     16

<210> SEQ ID NO 21
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(5)
<223> OTHER INFORMATION: a, c, g or t
<220> FEATURE:
<221> NAME/KEY: modified_base
<222> LOCATION: (10)..(10)
<223> OTHER INFORMATION: a, c, g or t
<220> FEATURE:
<221> NAME/KEY: modified_base
<222> LOCATION: (13)..(13)
<223> OTHER INFORMATION: a, c, g or t

<400> SEQUENCE: 21
wgtgnagwan canaga                                                    16

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, g or t
<220> FEATURE:
<221> NAME/KEY: modified_base
<222> LOCATION: (11)..(11)
<223> OTHER INFORMATION: a, c, g or t

<400> SEQUENCE: 22
gtncgaswca nawgtt                                                    16

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaacatcttc ttcgtcagcc atttggtcaa                                     30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggttcttcag atcatcataa attggagcta                                     30

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
```

```
atggctggtg cttcttcttt gg                                              22
```

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
tctctccgac agatgtgtca gg                                              22
```

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
catggcaact ctatttctca c                                               21
```

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
cgtcaccgtc aagatcagtt cc                                              22
```

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
atggttagtc agaaagagac cg                                              22
```

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
gacacgaaat acatccatcc tg                                              22
```

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctcaacaatg tcttcatcca acgcct                                        26

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgaaaacgca accgtaagag ag                                            22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gccggagagt ctaagctcaa ct                                            22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccacggcctg atgatcagca tt                                            22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gatggttgcg gttgaaagag tt                                            22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aaagcgctta catcggtgtg ag                                            22

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggatccatgg ttgtgaaagt gcatgg                                        26

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gagctcgtcc cgtactccac aacaat                                              26

<210> SEQ ID NO 39
<211> LENGTH: 214
<212> TYPE: PRT
<213> ORGANISM: Arabidopsis thaliana

<400> SEQUENCE: 39

Met Val Val Lys Val Tyr Gly Gln Ile Lys Ala Ala Asn Pro Gln Arg
1               5                   10                  15

Val Leu Leu Cys Phe Leu Glu Lys Asp Ile Glu Phe Glu Val Ile His
            20                  25                  30

Val Asp Leu Asp Lys Leu Glu Gln Lys Lys Pro Gln His Leu Leu Arg
        35                  40                  45

Gln Pro Phe Gly Gln Val Pro Ala Ile Glu Asp Gly Tyr Leu Lys Leu
    50                  55                  60

Phe Glu Ser Arg Ala Ile Ala Arg Tyr Tyr Ala Thr Lys Tyr Ala Asp
65                  70                  75                  80

Gln Gly Thr Asp Leu Leu Gly Lys Thr Leu Glu Gly Arg Ala Ile Val
                85                  90                  95

Asp Gln Trp Val Glu Val Glu Asn Asn Tyr Phe Tyr Ala Val Ala Leu
            100                 105                 110

Pro Leu Val Met Asn Val Phe Lys Pro Lys Ser Gly Lys Pro Cys
        115                 120                 125

Asp Val Ala Leu Val Glu Glu Leu Lys Val Lys Phe Asp Lys Val Leu
    130                 135                 140

Asp Val Tyr Glu Asn Arg Leu Ala Thr Asn Arg Tyr Leu Gly Gly Asp
145                 150                 155                 160

Glu Phe Thr Leu Ala Asp Leu Ser His Met Pro Gly Met Arg Tyr Ile
                165                 170                 175

Met Asn Glu Thr Ser Leu Ser Gly Leu Val Thr Ser Arg Glu Asn Leu
            180                 185                 190

Asn Arg Trp Trp Asn Glu Ile Ser Ala Arg Pro Ala Trp Lys Lys Leu
        195                 200                 205

Met Glu Leu Ala Ala Tyr
    210

<210> SEQ ID NO 40
<211> LENGTH: 232
<212> TYPE: PRT
<213> ORGANISM: Petunia sp.

<400> SEQUENCE: 40

Met Val Val Lys Val His Gly Ser Ala Met Ala Cys Pro Gln Arg
1               5                   10                  15

Val Met Val Cys Leu Ile Glu Leu Gly Val Asp Phe Glu Leu Ile His
            20                  25                  30

Val Asp Leu Asp Ser Leu Glu Gln Lys Lys Pro Glu Phe Leu Val Leu

```
                35                  40                  45
Gln Pro Phe Gly Gln Val Pro Val Ile Glu Asp Gly Asp Phe Arg Leu
         50                  55                  60

Phe Glu Ser Arg Ala Ile Ile Arg Tyr Tyr Ala Ala Lys Tyr Glu Val
 65                  70                  75                  80

Lys Gly Ser Lys Leu Thr Gly Thr Thr Leu Glu Glu Lys Ala Leu Val
                 85                  90                  95

Asp Gln Trp Leu Glu Val Glu Ser Asn Tyr Asn Asp Leu Val Tyr
             100                 105                 110

Asn Met Val Leu Gln Leu Leu Val Phe Pro Lys Met Gly Gln Thr Ser
            115                 120                 125

Asp Leu Thr Leu Val Thr Lys Cys Ala Asn Lys Leu Glu Asn Val Phe
        130                 135                 140

Asp Ile Tyr Glu Gln Arg Leu Ser Lys Ser Lys Tyr Leu Ala Gly Glu
145                 150                 155                 160

Phe Phe Ser Leu Ala Asp Leu Ser His Leu Pro Ser Leu Arg Phe Leu
                165                 170                 175

Met Asn Glu Gly Gly Phe Ser His Leu Val Thr Lys Arg Lys Cys Leu
            180                 185                 190

His Glu Trp Tyr Leu Asp Ile Ser Ser Arg Asp Ser Trp Lys Lys Val
        195                 200                 205

Leu Asp Leu Met Met Lys Lys Ile Ser Glu Ile Glu Ala Val Ser Ile
210                 215                 220

Pro Ala Lys Glu Glu Ala Lys Val
225                 230

<210> SEQ ID NO 41
<211> LENGTH: 213
<212> TYPE: PRT
<213> ORGANISM: Nicotiana tabacum

<400> SEQUENCE: 41

Met Ala Ile Lys Val His Gly Ser Pro Met Ser Thr Ala Thr Met Arg
 1               5                  10                  15

Val Ala Ala Cys Leu Ile Glu Lys Glu Leu Asp Phe Glu Phe Val Pro
             20                  25                  30

Val Asp Met Ala Ser Gly Glu His Lys Lys His Pro Tyr Leu Ser Leu
         35                  40                  45

Asn Pro Phe Gly Gln Val Pro Ala Phe Glu Asp Gly Asp Leu Lys Leu
     50                  55                  60

Phe Glu Ser Arg Ala Ile Thr Gln Tyr Ile Ala His Val Tyr Ala Asp
 65                  70                  75                  80

Asn Gly Tyr Gln Leu Ile Leu Gln Asp Pro Lys Lys Met Pro Ser Met
                 85                  90                  95

Ser Val Trp Met Glu Val Glu Gly Gln Lys Phe Glu Pro Pro Ala Thr
            100                 105                 110

Lys Leu Thr Trp Glu Leu Gly Ile Lys Pro Ile Ile Gly Met Thr Thr
        115                 120                 125

Asp Asp Ala Val Lys Glu Ser Glu Ala Gln Leu Ser Lys Val Leu
            130                 135                 140

Asp Ile Tyr Glu Thr Gln Leu Ala Glu Ser Lys Tyr Leu Gly Gly Asp
145                 150                 155                 160

Ser Phe Thr Leu Val Asp Leu His His Ile Pro Asn Ile Tyr Tyr Leu
                165                 170                 175
```

```
Met Ser Ser Lys Val Lys Glu Val Phe Asp Ser Arg Pro Arg Val Ser
            180                 185                 190

Ala Trp Cys Ala Asp Ile Leu Ala Arg Pro Ala Trp Val Lys Gly Leu
        195                 200                 205

Glu Lys Leu Gln Lys
    210

<210> SEQ ID NO 42
<211> LENGTH: 222
<212> TYPE: PRT
<213> ORGANISM: Zea mays

<400> SEQUENCE: 42

Met Ala Pro Leu Lys Leu Tyr Gly Met Pro Leu Ser Pro Asn Val Val
1               5                   10                  15

Arg Val Ala Thr Val Leu Asn Glu Lys Gly Leu Asp Phe Glu Ile Val
            20                  25                  30

Pro Val Asp Leu Thr Thr Gly Ala His Lys Gln Pro Asp Phe Leu Ala
        35                  40                  45

Leu Asn Pro Phe Gly Gln Ile Pro Ala Leu Val Asp Gly Asp Glu Val
50                  55                  60

Leu Phe Glu Ser Arg Ala Ile Asn Arg Tyr Ile Ala Ser Lys Tyr Ala
65                  70                  75                  80

Ser Glu Gly Thr Asp Leu Leu Pro Ala Thr Ala Ser Ala Ala Lys Leu
                85                  90                  95

Glu Val Trp Leu Glu Val Glu Ser His His Phe His Pro Asn Ala Ser
            100                 105                 110

Pro Leu Val Phe Gln Leu Leu Val Arg Pro Leu Leu Gly Gly Ala Pro
        115                 120                 125

Asp Ala Ala Val Val Glu Lys His Ala Glu Gln Leu Ala Lys Val Leu
130                 135                 140

Asp Val Tyr Glu Ala His Leu Ala Arg Asn Lys Tyr Leu Ala Gly Asp
145                 150                 155                 160

Glu Phe Thr Leu Ala Asp Ala Asn His Ala Leu Leu Pro Ala Leu Thr
                165                 170                 175

Ser Ala Arg Pro Pro Arg Pro Gly Cys Val Ala Ala Arg Pro His Val
            180                 185                 190

Lys Ala Trp Trp Glu Ala Ile Ala Ala Arg Pro Ala Phe Gln Lys Thr
        195                 200                 205

Val Ala Ala Ile Pro Leu Pro Pro Pro Ser Ser Ser Ala
    210                 215                 220

<210> SEQ ID NO 43
<211> LENGTH: 214
<212> TYPE: PRT
<213> ORGANISM: Zea mays

<400> SEQUENCE: 43

Met Ala Pro Met Lys Leu Tyr Gly Ala Val Met Ser Trp Asn Leu Thr
1               5                   10                  15

Arg Cys Ala Thr Ala Leu Glu Glu Ala Gly Ser Asp Tyr Glu Ile Val
            20                  25                  30

Pro Ile Asn Phe Ala Thr Ala Glu His Lys Ser Pro Glu His Leu Val
        35                  40                  45

Arg Asn Pro Phe Gly Gln Val Pro Ala Leu Gln Asp Gly Asp Leu Tyr
50                  55                  60
```

```
Leu Phe Glu Ser Arg Ala Ile Cys Lys Tyr Ala Ala Arg Lys Asn Lys
 65                  70                  75                  80

Pro Glu Leu Leu Arg Glu Gly Asn Leu Glu Ala Ala Met Val Asp
                 85                  90                  95

Val Trp Ile Glu Val Ala Asn Gln Tyr Thr Ala Ala Leu Asn Pro
            100                 105                 110

Ile Leu Phe Gln Val Leu Ile Ser Pro Met Leu Gly Gly Thr Thr Asp
            115                 120                 125

Gln Lys Val Val Asp Glu Asn Leu Glu Lys Leu Lys Lys Val Leu Glu
    130                 135                 140

Val Tyr Glu Ala Arg Leu Thr Lys Cys Lys Tyr Leu Ala Gly Asp Phe
145                 150                 155                 160

Leu Ser Leu Ala Asp Leu Asn His Val Ser Val Thr Leu Cys Leu Phe
                165                 170                 175

Ala Thr Pro Tyr Ala Ser Val Leu Asp Ala Tyr Pro His Val Lys Ala
            180                 185                 190

Trp Trp Ser Gly Leu Met Glu Arg Pro Ser Val Gln Lys Val Ala Ala
        195                 200                 205

Leu Met Lys Pro Ser Ala
    210

<210> SEQ ID NO 44
<211> LENGTH: 223
<212> TYPE: PRT
<213> ORGANISM: Zea mays

<400> SEQUENCE: 44

Met Ala Thr Pro Ala Val Lys Val Tyr Gly Trp Ala Ile Ser Pro Phe
1               5                   10                  15

Val Ser Arg Ala Leu Leu Ala Leu Glu Glu Ala Gly Val Asp Tyr Glu
            20                  25                  30

Leu Val Pro Met Ser Arg Gln Asp Gly Asp His Arg Pro Glu His
        35                  40                  45

Leu Ala Arg Asn Pro Phe Gly Lys Val Pro Val Leu Glu Asp Gly Asp
50                  55                  60

Leu Thr Leu Phe Glu Ser Arg Ala Ile Ala Arg His Val Leu Arg Lys
65                  70                  75                  80

His Lys Pro Glu Leu Leu Gly Gly Arg Leu Glu Gln Thr Ala Met
                85                  90                  95

Val Asp Val Trp Leu Glu Val Glu Ala His Gln Leu Ser Pro Pro Ala
            100                 105                 110

Ile Ala Ile Val Val Glu Cys Val Phe Ala Pro Phe Leu Gly Arg Glu
            115                 120                 125

Arg Asn Gln Ala Val Val Asp Glu Asn Val Glu Lys Leu Lys Lys Val
    130                 135                 140

Leu Glu Val Tyr Glu Ala Arg Leu Ala Thr Cys Thr Tyr Leu Ala Gly
145                 150                 155                 160

Asp Phe Leu Ser Leu Ala Asp Leu Ser Pro Phe Thr Ile Met His Cys
                165                 170                 175

Leu Met Ala Thr Glu Tyr Ala Ala Leu Val His Ala Leu Pro His Val
            180                 185                 190

Ser Ala Trp Trp Gln Gly Leu Ala Ala Arg Pro Ala Ala Asn Lys Val
        195                 200                 205

Ala Gln Phe Met Pro Val Gly Ala Gly Ala Pro Lys Glu Gln Glu
    210                 215                 220
```

<210> SEQ ID NO 45
<211> LENGTH: 229
<212> TYPE: PRT
<213> ORGANISM: Triticum sp.

<400> SEQUENCE: 45

Met Ser Pro Val Lys Val Phe Gly His Pro Met Leu Thr Asn Val Ala
1               5                   10                  15

Arg Val Leu Leu Phe Leu Glu Glu Val Gly Ala Glu Tyr Glu Leu Val
            20                  25                  30

Pro Met Asp Phe Val Ala Gly Glu His Lys Arg Pro Gln His Val Gln
        35                  40                  45

Leu Asn Pro Phe Ala Lys Met Pro Gly Phe Gln Asp Gly Asp Leu Val
    50                  55                  60

Leu Phe Glu Ser Arg Ala Ile Ala Lys Tyr Ile Leu Arg Lys Tyr Gly
65                  70                  75                  80

Gly Thr Ala Gly Leu Asp Leu Gly Glu Asn Ser Gly Ile Glu Glu
                85                  90                  95

Leu Ala Met Val Asp Val Trp Thr Glu Val Glu Ala Gln Gln Tyr Tyr
            100                 105                 110

Pro Ala Ile Ser Pro Val Val Phe Glu Cys Ile Ile Ile Pro Phe Ile
        115                 120                 125

Ile Pro Gly Gly Gly Ala Ala Pro Asn Gln Thr Val Val Asp Glu Ser
    130                 135                 140

Leu Glu Arg Leu Arg Gly Val Leu Gly Ile Tyr Glu Ala Arg Leu Glu
145                 150                 155                 160

Lys Ser Arg Tyr Leu Ala Gly Asp Ser Ile Thr Phe Ala Asp Leu Asn
                165                 170                 175

His Ile Pro Phe Thr Phe Tyr Phe Met Thr Thr Pro Tyr Ala Lys Val
            180                 185                 190

Phe Asp Asp Tyr Pro Lys Val Lys Ala Trp Trp Glu Met Leu Met Ala
        195                 200                 205

Arg Pro Ala Val Gln Arg Val Cys Lys His Met Pro Thr Glu Phe Lys
    210                 215                 220

Leu Gly Ala Gln Tyr
225

<210> SEQ ID NO 46
<211> LENGTH: 236
<212> TYPE: PRT
<213> ORGANISM: Zea mays

<400> SEQUENCE: 46

Met Arg Val Leu Gly Gly Glu Val Ser Pro Phe Thr Ala Arg Ala Arg
1               5                   10                  15

Leu Ala Leu Asp Leu Arg Gly Val Ala Tyr Glu Leu Leu Asp Glu Pro
            20                  25                  30

Leu Gly Pro Lys Lys Ser Asp Arg Leu Leu Ala Ala Asn Pro Val Tyr
        35                  40                  45

Gly Lys Ile Pro Val Leu Leu Leu Pro Asp Gly Arg Ala Ile Cys Glu
    50                  55                  60

Ser Ala Val Ile Val Gln Tyr Ile Glu Asp Val Ala Arg Glu Ser Gly
65                  70                  75                  80

Gly Ala Glu Ala Gly Ser Leu Leu Leu Pro Asp Pro Tyr Glu Arg
                85                  90                  95

-continued

```
Ala Met His Arg Phe Trp Thr Ala Phe Ile Asp Asp Lys Phe Trp Pro
            100             105             110

Ala Leu Asp Ala Val Ser Leu Ala Pro Thr Pro Gly Ala Arg Ala Gln
            115             120             125

Ala Ala Glu Asp Thr Arg Ala Ala Leu Ser Leu Leu Glu Glu Ala Phe
        130             135             140

Lys Asp Arg Ser Asn Gly Arg Ala Phe Phe Ser Gly Gly Asp Ala Ala
145             150             155             160

Pro Gly Leu Leu Asp Leu Ala Leu Gly Cys Phe Leu Pro Ala Leu Arg
                165             170             175

Ala Cys Glu Arg Leu His Gly Leu Ser Leu Ile Asp Ala Ser Ala Thr
            180             185             190

Pro Leu Leu Asp Gly Trp Ser Gln Arg Phe Ala Ala His Pro Ala Ala
            195             200             205

Lys Arg Val Leu Pro Asp Thr Glu Lys Val Val Gln Phe Thr Arg Phe
        210             215             220

Leu Gln Val Gln Ala Gln Phe Arg Val His Val Ser
225             230             235
```

PLANT PIGMENT ACCUMULATION GENE

This application is based upon and claims the benefit of priority from Japanese Patent Application No. 2003-066310 filed Mar. 12, 2003, the entire contents of this application are incorporated herein by reference.

BACKGROUND OF THE INVENTION

This invention relates to a protein having the activity for vacuolar compartmentalization of flavonoids in plant cells, as well as a gene encoding the protein. The invention also relates to a transformed plant harboring the gene.

Flavonoids are the secondary metabolites unique in the plant kingdom. They include three major subclasses of compounds: flavonols, anthocyanins, and proanthocyanidins (PAs; so-called condensed tannins). Despite the multitude of functions of flavonoids in plants such as UV-B protectants, signaling molecules between plants and microbes, and regulators of auxin transport (reviewed in Winkel-Shirley, B. (2001) Plant Physiol. 126, 485-493), loss or deficiency in flavonoids has generally no deleterious effect on plant growth and development, and is easily detected as a change of color in some specific organs. These facts prompted the present inventors to isolate mutants with reduced or varied coloration in order to uncover the flavonoid biosynthetic pathway in plants.

Changes in flavonoid pigments in maize kernels are one of the topics most intensively studied so far, which contributed to the establishment of anthocyanin pathway. Given the purpose of molecular breeding in ornamental plant species, a number of mutants have been isolated in petunia and snapdragon (Mol, J., Grotewold, E., and Koes, R. (1998) Trends Plant Sci. 3, 212-217). Over the last decade molecular genetics in Arabidopsis has been developed. Most Arabidopsis mutants deficient in flavonoid pigments have been described as transparent testa (tt) (Koornneef, M. (1990) Arabidopsis Inf. Serv. 27, 1-4).

To date, 21 tt loci have been identified, and about a half of them have been analyzed in detail. Analysis on the tt mutants achieved cloning and characterization of a number of structural and regulatory genes in Arabidopsis flavonoid pathway (FIG. 1). Because the structural genes are single-copy except for flavonol synthase (FLS), the Arabidopsis flavonoid biosynthetic pathway is valuable as a model to analyze regulation and subcellular organization for plant metabolisms (reviewed in Winkel-Shirley, B. (1999) Physiol. Plant. 107, 142-149).

The flavonoid synthesis proceeds in the cytosol, whereas most of their endproducts are finally accumulated in the vacuoles. Because many secondary metabolites including flavonoids are cytotoxic and genotoxic even in the cells that produce them, it is thought that there is a sequestration system that is analogous or related to that for exogenous toxic compounds in plants. Detoxification of xenobiotics in plants is composed of three phases: (I) activation phase which usually involves hydrolysis or oxidation to realize higher reactivity, (II) conjugation phase of compounds metabolized in phase I with hydrophilic molecules such as glucose, malonate or glutathione, and (III) export phase from the cytosol by membrane-associated transport proteins (Coleman, J. O. D., et al (1997) Trends Plant Sci. 2, 144-151).

Major reaction in phase I is catalyzed by the cytochrome P-450, and some P-450 enzymes are involved in the flavonoid biosynthetic pathway such as cinnamate 4-hydroxylase, F3'H, F3'5'H (Winkel-Shirley, 2001, supra). With respect to detoxification of anthocyanins, conjugation with glucosyl moieties at 3 position is necessary to solubilize the precursors (anthocyanidins), and it is said that the corresponding transferase, UDP-glucose:flavonoid glucosyltransferase (UFGT), is one of the structural enzymes in anthocyanin pathway. Based on the structures of anthocyanins identified to date, they must undergo various modifications such as methylation, acylation, and glycosylation, and some corresponding genes have been identified in petunia (e.g., Brugliera, F., et al. (1994) Plant J. 5, 81-92).

In addition, it was reported that glutathione S-transferase (GST) is essential for anthocyanin pigmentation. Maize BZ2 and petunia AN9 encode GST proteins, and they can functionally complement each other (Alfenito, M. R., et al., (1998) Plant Cell 10, 1135-1149). The function of these GSTs was firstly thought to be the one of forming glutathione-conjugates of anthocyanidin-3-glucosides (Marrs, K. A., et al. (1995) Nature 375, 397-400).

In comparison with anthocyanins, modification and compartmentalization of PAs or their precursors are more poorly understood. The current hypothetical model for PA accumulation mechanisms depends largely on the data from Douglas fir (reviewed in Stafford, H. A. (1989). The enzymology of proanthocyanidin biosynthesis. In Chemistry and significance of condensed tannins (Hemingway, R. W. and Karchesy J. J. eds). New York: Plenum Press, pp. 47-70.).

It has been believed that PAs are composed of flavan 3-ols and flavan 3,4-diols (leucoanthocyanidins), the former of which as start units and the latter as extension units, but another pathway involving 2,3-cis-flavan 3-ols as extension units was recently suggested (Xie, D.-Y., et al. (2003) Science 299, 396-399: FIG. 1).

It is likely that their uptake into the vacuoles (or the lumen of the endoplasmic reticulum; Stafford, 1989, supra) is performed as monomer forms but not as polymer forms (Debeaujon, I., et al. (2001) Plant Cell 13, 853-871). The precursors are progressively condensed and the polymers formed are oxidized, resulting in brown coloration (FIG. 1).

The condensation and oxidation steps are probably performed enzymatically, while non-enzymatic reactions can be easily done (Stafford, 1989, supra). Some barley mutants presumably involved in condensing and/or accumulation steps were reported as tannnin (proanthocyanidin)-deficient (ant) mutants (Gruber, M. Y., et al., (1999) Genetic systems for condensed tannin biotechnology. In Plant Polyphenols 2: Chemistry and Biology. (Gross, G. G., Hemingway, R. W., and Yoshida, T. eds). New York: Kluwer Academic/Plenum Publishers, pp. 315-341), but molecular and biochemical evidence for their compartmentalization, polymerization and oxidation after the synthesis of PA precursors has to be awaited.

In Arabidopsis, compartmentalization mechanisms for flavonoids, even for anthocyanins, remain to be clarified, as compared with their biosynthetic pathway (FIG. 1). This situation is accounted for mainly by the fact that most of tt mutants are restricted to those which are defective in flavonoid 'synthetic' steps but not in 'transport' steps. The exception is the case of tt12 mutant. Debeaujon et al. (2001. supra) have isolated TT12 gene and suggested that TT12 is a putative transporter, which is responsible, at least in part, for vacuolar sequestration of PA precursors in Arabidopsis seed coat.

The present inventors previously obtained two novel tt mutants during investigation of mutation rate of ion beam irradiation in Arabidopsis (Shikazono, N., et al. (2003) Genetics 163, 1449-1455). One is a tt18 mutant (formerly named as tt19 in Winkel-Shirley, 2001, supra), in which a gene encoding a putative leucoanthocyanidin dioxygenase (LDOX) is impaired. The other is defined as a tt19 mutant, but to date, neither the causative gene nor the nature of the tt19 mutant has been elucidated.

SUMMARY OF THE INVENTION

The present invention has been accomplished under these circumstances and has as an object analyzing the characteristics of the tt19 mutant, identifying the causative gene which induces the tt19 mutant and analyzing its nature.

Another object of the invention is to provide a transformed plant by making use of the nature of the identified causative gene.

The present inventors conducted extensive studies with a view to attaining those objects by analyzing the causative gene of the tt19 mutant and elucidating the nature of the tt19 mutant. As a result, they cloned a novel gene designated the TRANSPARENT TESTA 19 (TT19) gene and analyzed both the DNA nucleotide sequence of the gene and the protein encoded by the DNA of that TT19 gene, which eventually led to the accomplishment of the present invention.

Thus, in one aspect of the present invention, there is provided a nucleic acid encoding a protein having the activity for vacuolar compartmentalization of flavonoids in plant cells. Included in the scope of the above-mentioned nucleic acid of the invention are: (i) a nucleic acid containing the nucleotide sequence represented by SEQ ID NO:1 or a nucleotide sequence which is degenerate with respect to SEQ ID NO:1; (ii) a nucleic acid containing a nucleotide sequence which is identical to SEQ ID NO:1 except that it has deletions, substitutions or additions of one or more bases; (iii) a nucleic acid containing a nucleotide sequence hybridizable under stringent conditions with a nucleotide sequence complementary to the nucleotide sequence represented by SEQ ID NO:1; and (iv) a nucleic acid containing a nucleotide sequence having at least 60%, preferably at least 70%, more preferably at least 80%, most preferably at least 90%, nucleotide sequence identity to the nucleotide sequence represented by SEQ ID NO:1.

In another aspect of the invention, there is also provided a nucleic acid that has a nucleotide sequence encoding a protein having the activity for vacuolar compartmentalization of flavonoids in plant cells and which is selected from the group consisting of: (a) a nucleic acid encoding a protein having the amino acid sequence represented by SEQ ID NO:2; (b) a nucleic acid encoding a protein having an amino acid sequence which is identical to SEQ ID NO:2 except that it has deletions, substitutions or additions of one or more amino acids; and (c) a nucleic acid encoding a protein having an amino acid sequence that has at least 60%, preferably at least 70%, more preferably at least 80%, most preferably at least 90%, amino acid sequence identity to the amino acid sequence represented by SEQ ID NO:2.

The present invention also provides a protein that is encoded by one of the nucleic acids described under (i)-(iv) or one of the nucleic acids described under (a)-(c) and which has the activity for vacuolar compartmentalization of flavonoids in plant cells.

In yet another embodiment of the invention, there are provided a recombinant vector containing one of the nucleic acids described under (i)-(iv) or one of the nucleic acids described under (a)-(c), as well as a transformed plant cell containing such recombinant vector.

In still another embodiment of the invention, there is provided a transgenic plant containing one of the nucleic acids described under (i)-(iv) or one of the nucleic acids described under (a)-(c).

In a further embodiment of the invention, there is provided a process for producing flavonoids which comprises the steps of cultivating the above-mentioned transformed plant cell in a culture medium or growing the above-mentioned transgenic plant and harvesting a vacuolarly accumulated flavonoid from the cultured transformed plant cell or the grown transgenic plant.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
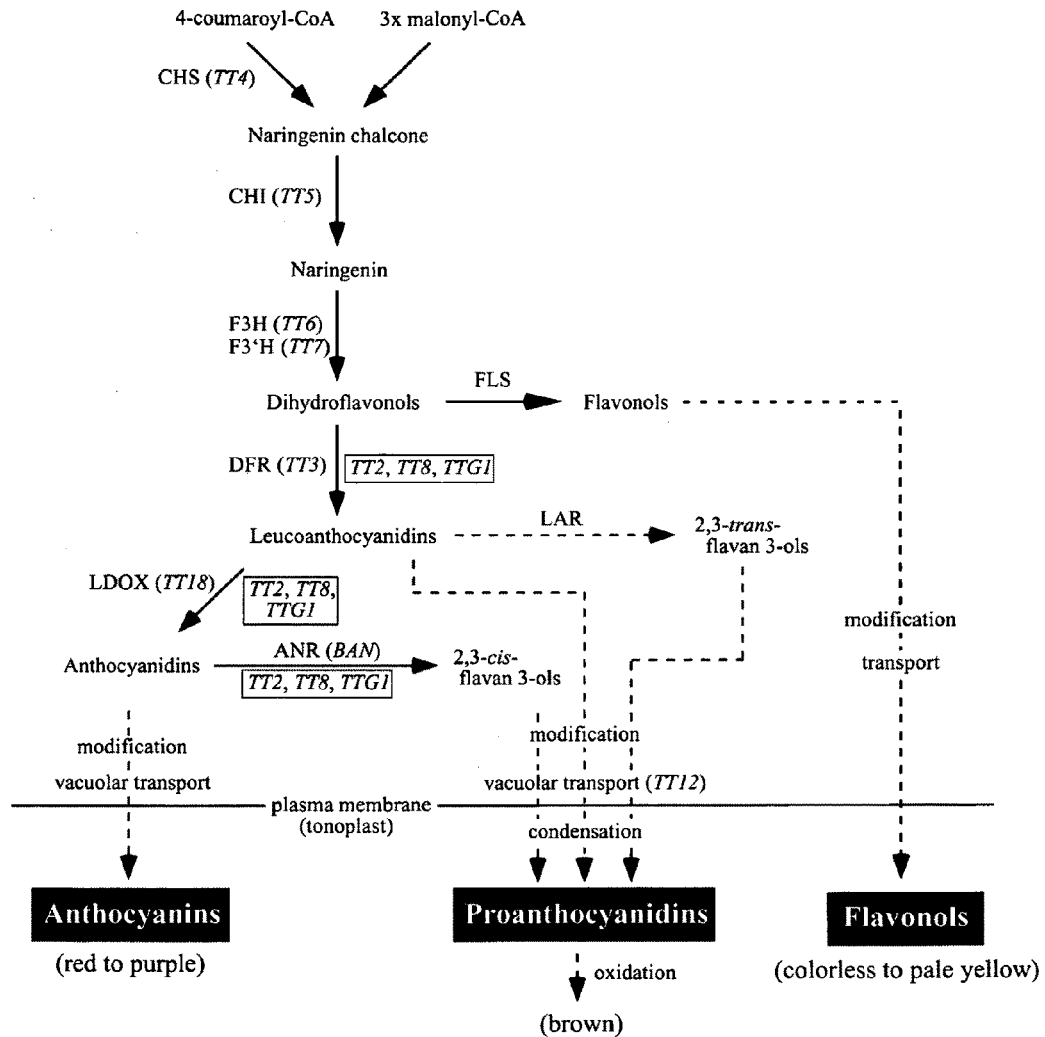
FIG. 1 shows flavonoid biosynthetic and accumulation pathways in Arabidopsis; enzymes catalyzing respective steps are indicated, with the corresponding genetic loci put in parentheses; regulatory loci are given in boxes; putative steps are shown as dotted arrows; it should be noted that anthocyanins and proanthocyanidins are accumulated in the vacuole, but a part of flavonols is secreted to the cell wall; CHS refers to chalcone synthase; CHI, chalcone isomerase; F3H, flavanone 3-hydroxylase; F3'H, flavonoid 3'-hydroxylase; DFR, dihydroflavonol 4-reductase; FLS, flavonol synthase; LDOX, leucoanthocyanidin dioxygenase; LAR, leucoanthocyanidin reductase; ANR, anthocyanidin reductase; TT, TRANSPARENT TESTA; TTG, TRANSPARENT TESTA GLABRA; and BAN, BANYULS.

The present inventors irradiated ion beams to dry seeds of Arabidopsis thaliana to obtain Arabidopsis mutants defined as tt19 mutants. The inventors then identified the causative gene of the mutants and elucidated the nature of the tt19 mutants. The tt19 mutants of interest to the present invention are characterized as having no pigmentation in the basal region of stem or in rosette leaves, and having no brown pigments in seed coat. This is probably because flavonoid pigments do not accumulate in the stem, leaves or seed coat. However, visual analysis alone is not capable of deciding on whether the failure in flavonoid accumulation is due to a mutation in genes involved in flavonoid synthesis or in genes involved in flavonoid transport or accumulation.

For further verification, the present inventors first made studies in order to identify the causative gene. As it turned out, translocational mutation occurred in the tt19 mutants. In Arabidopsis thaliana ecotype Columbia (Col) ecotype, the inventors analyzed the locus region where the translocational mutation had occurred in the tt19 mutants, thereby analyzing the gene that had undergone mutation in the tt19 mutants. As a result, the gene which had caused mutation in the tt19 mutants was found to be such that it has a nucleotide sequence having the 645-bp open reading frame represented by SEQ ID NO:1 and encodes a protein composed of 214 amino acids having the amino acid sequence represented by SEQ ID NO:2; this gene was designated TT19 gene.

The present inventors analyzed the nucleotide sequence of the TT19 gene and the amino acid sequence of the TT19 protein by Clustal W, ver. 1.7 (Thompson, J. D., et al. (1994) Nucleic Acids Res. 22, 4673-4680). At the mRNA level, the nucleotide sequence identity was about 55% as compared with the nucleotide sequence of petunia AN9 gene, about 40% with the nucleotide sequence of maize BZ2 gene, and about 75% with the nucleotide sequence of Arabidopsis thaliana EST clone H36860; at the protein level, the amino acid sequence identity was about 70% as compared with the amino acid sequence of H36860, about 50% with the amino acid sequence of petunia AN9, and about 15% with the amino acid sequence of maize BZ2. The petunia AN9 gene and the maize BZ2 gene are each glutathione S-transferase (GST) gene which is known to be necessary for anthocyanin pigmentation in petunia and maize, respectively. From these, it was speculated that the TT19 gene under consideration is the GST-like gene necessary for anthocyanin pigmentation.

Then, in order to analyze the functions of the identified TT19 gene, the inventors transformed tt19 mutants with an expression vector containing the TT19 gene and its authentic promoter; as it turned out, the pigmentation in the basal region of stem and rosette leaves that was observed in Arabidopsis thaliana ecotype Col ecotype, as well as the deposition of brown pigments in seed coat were restored. A further study was made on the function of TT19; when the TT19 gene was mutated, flavonoid synthesis was normal but the synthesized flavonoids were not normally accumulated in intracellular vacuoles, thus making it clear that the TT19 protein is required for vacuolar compartmentalization of flavonoid pigments.

Speaking of the petunia AN9 homologous to the TT19 of the present invention at both the nucleotide and amino acid levels, it was already known as the molecule necessary for vacuolar compartmentalization of anthocyanins in petunia, so the present inventors transformed Arabidopsis thaliana tt19 mutants with the AN9 gene under the control of potent cauliflower mosaic virus (CaMV) 35S promoter in order to see whether the AN9 gene would complement the function of TT19. As it turned out, transformation with the AN9 gene restored the vacuolar compartmentalization of anthocyanins but not the vacuolar compartmentalization of other flavonoids such as anthocyanidins; it therefore became clear that the function of the TT19 gene is not completely complemented by the AN9 gene.

On the basis of the above results, the present invention can provide a nucleic acid having a nucleotide sequence that encodes a protein having the activity for vacuolar compartmentalization of flavonoids in plant cells, and included in the scope of the nucleic acid of the invention are:

(i) a nucleic acid containing the nucleotide sequence represented by SEQ ID NO:1 or a nucleotide sequence which is degenerate with respect to SEQ ID NO:1;

(ii) a nucleic acid containing a nucleotide sequence which is identical to SEQ ID NO:1 except that it has deletions, substitutions or additions of one or more bases;

(iii) a nucleic acid containing a nucleotide sequence hybridizable under stringent conditions with a nucleotide sequence complementary to the nucleotide sequence represented by SEQ ID NO:1;

(iv) a nucleic acid containing a nucleotide sequence having at least 60%, preferably at least 70%, more preferably at least 80%, most preferably at least 90%, nucleotide sequence identity to the nucleotide sequence represented by SEQ ID NO:1;

(a) a nucleic acid encoding a protein having the amino acid sequence represented by SEQ ID NO:2;

(b) a nucleic acid encoding a protein having an amino acid sequence which is identical to SEQ ID NO:2 except that it has deletions, substitutions or additions of one or more amino acids; and (c) a nucleic acid encoding a protein having an amino acid sequence that has at least 60%, preferably at least 70%, more preferably at least 80%, most preferably at least 90%, amino acid sequence identity to the amino acid sequence represented by SEQ ID NO:2.

The term "flavonoid" or "flavonoids" as used herein covers anthocyanins, anthocyanidins, tannins, etc., and the expression "the activity for vacuolar compartmentalization of flavonoids" refers to the activity by which flavonoids synthesized in such plant cells as petals, leaves, stems, roots and seeds are accumulated in their vacuoles so that they will neither flow into the cytoplasm nor leak out of the cell.

The term "one or more" as used in the invention preferably refers to between one and twenty, more preferably between one and ten, and most preferably between one and five. Nucleic acids having "deletions", "substitutions" or "additions" of one or more bases in the invention are those nucleic acids which occur in the nucleotide sequence of the TT19 gene (SEQ ID NO:1) and encode proteins having similar properties to the TT19 protein. Proteins having "deletions", "substitutions" or "additions" of one or more amino acids in the invention are those proteins which have similar properties to the TT19 protein (SEQ ID NO:2). The "substitution" of amino acids may be exemplified by the substitutions of one amino acid by another having similar properties, for example, the substitution of a certain hydrophobic amino acid by another hydrophobic amino acid, the substitution of a certain hydrophilic amino acid by another hydrophilic amino acid, the substitution of a certain acidic amino acid by another acidic amino acid, and the substitution of a certain basic amino acid by another basic amino acid.

The above-described nucleotide sequences having "deletions", "substitutions" or "additions", as well as the above-described proteins having "deletions", "substitutions" or "additions" can be prepared by employing not only mutagenic treatments at the cellular level such as ion-beam irradiation and mutagen treatment but also various methods known in the technical field of the invention, such as genetically engineered mutagenic treatments exemplified by site-directed mutagenesis, random mutagenesis utilizing errors in PCR amplification and cassette mutagenesis.

The nucleotide sequences that encode proteins having the activity for vacuolar compartmentalization of flavonoids in plant cells according to the present invention include those nucleotide sequences which have DNA containing nucleotide sequences hybridizable under stringent conditions with a nucleotide sequence complementary to the nucleotide sequence of the TT19 gene (SEQ ID NO:1) and which encode proteins having the activity for vacuolar compartmentalization of flavonoids in plant cells.

The term "stringent conditions" as used in the invention refers to those conditions under which the nucleotide sequence of interest can hybridize specifically with the nucleotide sequence encoding the TT19 gene (e.g. SEQ ID NO:1) or a nucleotide sequence that is degenerate with respect to that nucleotide sequence. Hybridizing conditions are determined considering other conditions such as temperature and ion concentration and it is generally known that the higher the temperature and the lower the ion concentration, the higher the stringency that is required. Such stringent conditions can be set by any skilled artisan on the basis of disclosures as in Sambrook and Russel (Molecular Cloning: A Laboratory Manual, 3rd edition (2001)). As a specific example of such stringent conditions, one may think of employing the hybridizing conditions of 6×SSC, 5×Denhardt's, 0.1% SDS at 25-68° C. In this case, a more preferred hybridization temperature may be 45-68° C. (without formamide) or 25-50° C. (with 50% formamide).

In the present invention, sequence identity between two amino acids or nucleotide sequences may be determined by visual inspection or mathematical calculations. Alternatively, the sequence identity between two protein sequences may be determined by comparing the sequence information employing the GAP computer program available from at Wisconsin University, the Genetics Computer Group (UWGCG) on the basis of the algorithm of Needleman and Wunsch (J. Mol Biol., 48:443-453, 1970). Preferred default parameters in the GAP program include: (1) the scoring matrix blosum62, as described in Henikoff and Henikoff (Proc. Natl. Acad. Sci. USA, 89:10915-10919, 1992); (2) weighting by 12 gaps; (3) weighting by 4 gap lengths; and (4) no penalty for a terminal gap.

For analysis of the sequence identity between amino acids or nucleotide sequences in the present invention, other programs for sequence comparison common to the skilled artisan may be employed. For instance, determination can be made by comparison with the sequence information employing the BLAST program described in Altschul et al. (Nucl. Acids. Res. 25., p. 3389-3402, 1997). Specifically, in nucleotide sequence analysis, Query nucleotide sequence may be entered on the Nucleotide BLAST (BLASTN) program and checked against a nucleotide sequence database such as GenBank, EMBL or DDBJ. In amino acid sequence analysis, Query amino acid sequence may be entered on the Protein BLAST (BLASTP) program and checked against an amino acid sequence database such as GenBank CDS, PDB, Swiss Prot or PIR. The BLASTP program can be accessed on the Internet from the web site of National Center for Biotechnology Information (NCBI) or DNA Data Bank of Japan (DDBJ). The various conditions (parameters) for homology search by the BLAST programs are described in detail on those sites and although part of their settings can be changed as appropriate, search is usually made with default values. Other programs for sequence comparison common to the skilled artisan, such as Clustal W, ver. 1.7 (Thompson, J. D., et al., (1994), supra), may also be employed.

The present invention can also provide a protein that has the activity for vacuolar compartmentalization of flavonoids in plant cells, and included among the proteins of the invention are those which are encoded by the nucleic acids described under (i)-(iv) or the nucleic acids described under (a)-(c), as exemplified by a protein having the amino acid sequence depicted in SEQ ID NO:2.

The invention can also provide recombinant vectors containing the nucleic acids described under (i)-(iv) or the nucleic acids described under (a)-(c). Such recombinant vectors can be obtained by linking one of the nucleic acids of (i)-(iv) or one of the nucleic acids of (a)-(c) into a suitable vector. Any vector that can be replicated in a host cell may be employed in the invention and may be exemplified by plasmid DNA or phage DNA. Examples of the plasmid DNA include *E. coli* derived plasmids (e.g. pUC19 and pBR322), *Bacillus subtilis* derived plasmids (e.g. pAMα1) and yeast-derived plasmids (e.g. pGILDA and YAC), and examples of the phage DNA include λphages (e.g. λEMBL, λZAP and λgt10). In order to insert the aforementioned nucleic acids of (i)-(iv) or nucleic acids of (a)-(c) into these vectors, the vector is cleaved with a suitable restriction enzyme and one of the nucleic acids described in (i)-(iv) or one of the nucleic acids described in (a)-(c) that has been treated with a restriction enzyme which makes the same cleavage ends as the first mentioned restriction enzyme is inserted into the cleaved site of the vector.

In addition to the nucleic acids described in (i)-(iv) or the nucleic acids described in (a)-(c), the vectors may contain sequences for controlling the expression of those nucleic acids, sequences for promoting the uptake of the vectors into the genome (e.g. T-DNA sequence) and/or sequences of selection markers (e.g. dihydrofolate reductase gene, kanamycin resistance gene and hygromycin resistance gene). Sequences that can be used to control the expression of the above-mentioned nucleic acids include, for example, promoter, enhancer, splicing signal and poly(A) addition signal. In addition to the cauliflower mosaic virus derived 35S promoter which is commonly employed in plants, the skilled artisan may choose appropriate vectors depending on a specific object of vector transformation in plants; if the plant is the *Arabidopsis thaliana* flower, one may employ a promoter for an endogenous gene that can be expressed at high level in the *Arabidopsis thaliana* flower.

In the present invention, there is also provided a transformed plant cell containing the above-described recombinant vector. The transformed plant cell of the invention can be obtained by introducing the recombinant vector of the invention into a host plant cell. The plant cell to be transformed in the invention may derive from any parts of a plant body including leaves, petals, stems, roots and seeds, as well as cultured plant cells. The plants as the source of plant cells are not limited in any particular way and may include Cruciferae, Gramineae and Leguminosae.

In order to transform the aforementioned recombinant vectors in plant cells, one may employ transformation techniques known in the art, such as Agrobacterium-mediated gene transfer, electroporation, the particle-gun technique and the polyethylene glycol (PEG) method.

When Agrobacterium-mediated gene transfer is employed, a constructed plant expression vector may be introduced into a suitable strains of Agrobacterium, such as *Agrobacterium tumefaciens*, and the Agrobacterium is infected to aseptically cultured leaves of a host according to an appropriate procedure such as vacuum infiltration (Bechtold et al. (1993) C. R. Acad. Sci. Ser. III Sci. Vie, 316, 1194-1199) or floral dipping (Clough, S. J., and Bent, A. F. (1998). Plant J. 16, 735-743), thereby obtaining a transformed plant.

In the case of electroporation, an electroporation device equipped with a pulse controller is operated under conditions of 500-600 V, 1000 µF and 20 msec so as to transfer a gene of interest into the host.

In the case of the particle-gun technique, a plant body, a plant organ or a plant tissue may be employed either as such or in the form of a prepared slice. Alternatively, a protoplast may be prepared for use. The thus prepared samples may be treated with a gene transfer apparatus (e.g. BIOLISTIC POS 1000/He of BioRad). The treatment conditions vary with the plant or sample to be treated but typically a pressure of about 1000-1100 psi and a distance of about 5-10 cm are employed.

In the case of the polyethylene glycol (PEG) method, the primary practice consists of preparing a protoplast from cultured cells and adding PEG in the presence of calcium and phosphate so as to incorporate the protoplast into the DNA cells.

In order to see if the desired nucleic acid as selected from among (i)-(iv) or (a)-(c) has been successfully transformed in the plant cell, various techniques may be employed, for example, PCR, Southern hybridization and Northern hybridization. In the case of PCR, in order to confirm successful transformation, DNA is first prepared from the presumably transformed plant cell or, alternatively, cDNA is prepared after collecting mRNA, and with the thus prepared DNA or cDNA being used as a template, PCR is performed using primers so designed as to effect specific amplification of the desired nucleic acid.

According to another embodiment of the invention, the thus prepared plant cell is cultured for redifferentiation and growth to thereby create a transgenic plant containing one of the nucleic acids described in (i)-(iv) or one of the nucleic acids described in (a)-(c). In order to redifferentiate the plant cell to a plant body, either a plant hormone is removed from the culture medium or suitable concentrations of plant hormones such as auxin, cytokinin, gibberellin and abscisic acid are administered either alone or in combination.

In a further embodiment of the invention, there is provided a process for producing flavonoids which comprises the steps of cultivating the above-mentioned transformed plant cell in a culture medium or growing the above-mentioned transgenic plant and harvesting a vacuolarly accumulated flavonoid from the cultured transformed plant cell or the grown transgenic plant. For cultivation of plant cells, various media known in the art of plant cultivation may be employed, including an MS basal medium, an LS basal medium, a protoplast culture medium (a modification of the LS medium), etc. These media may be supplemented with additives such as sucrose, various vitamins, and amino acids.

For cultivation, either solid culture using a solid medium or liquid culture using a liquid medium may be employed. Specifically, the pH of the medium is adjusted to between 5.0 and 7.0 and culture is effected at about 20-30° C., preferably about 23-28° C., for 5 days to 2 months. For growing transgenic plants, various techniques may be employed, such as soil cultivation in a field or a greenhouse, hydroponics in a greenhouse, and an incubator.

The flavonoids accumulated vacuolarly in the cultured plant cells or transgenic plant can be harvested by collecting the vacuoles from the plant cells or transgenic plant or purifying the flavonoids from the obtained vacuoles. In the present invention, cell walls are lysed with an enzyme such as cellulase or pectinase, the cells are disrupted by sonication, homogenization, etc. in a solubilizing solution and, after removing the insoluble matter by filtration, centrifugation, etc., organic solvent fractions such as methanol, hexane or acetone are collected, thereby obtaining a solution containing flavonoid-carrying vacuoles from the plant cells or transgenic plant. In order to purify flavonoids from the thus prepared vacuoles, various chromatographic techniques (e.g. high performance liquid chromatography (HPLC), reverse-phase chromatography and gas chromatography (GC)) may be further applied either alone or in combination.

The following examples are provided for further illustrating the present invention but are in no way to be taken as limiting its technical scope.

EXAMPLES

Example 1

Creation of Plant Materials

Mutagenesis and isolation of tt19 mutants were previously described (Shikazono et al., 2003, supra). Briefly, dry seeds (26,000 grains) of *Arabidopsis thaliana* ecotype Columbia (Col) ecotype were irradiated with 150 Gy of accelerated carbon ion particles to generate mutants (Tanaka, A. et al., (1997a). Int. J. Radiat. Biol. 72, 121-127). From among the offspring after the second and subsequent generations of the treated seeds (100,000 individuals), those individuals which had undergone such changes as the loss of pigmentation in the basal region of the stem or rosette leaves and the loss of brown pigments at seed coat were selected as candidate mutants. Thereafter, those candidate mutants were analyzed in accordance with genetic, physiological and molecular biological techniques to isolate two M2 lineages that did not have any known mutations. These were allelic mutants and named tt19-1 mutant and tt19-2 mutant.

Ecotype Landsberg erecta (Ler) was used for molecular mapping of TT19 gene. In the Examples in the present specification, ast/ban-4 mutant and tt4(C1) mutant were used as negative controls (tt4(C1) mutant is hereunder referred to as "tt4 mutant") and had been created by previously described methods (ast/ban-4 by Tanaka, A. et al., (1997b). Genes Genet. Syst. 72, 141-148 and tt4 mutant by Shikazono, N. et al., (1998). Genes Genet. Syst. 73, 173-179). The ast/ban-4 mutant is a null mutant of the BAN gene that is deficient in both AST/BAN-4 alleles and the tt4 mutant is a null mutant of the TT4 gene that is deficient in both TT4 alleles. Each of these mutants has the Col background.

Example 2

Phenotypic Characterization of tt19 Mutants

The two tt19 mutants created in Example 1 (tt19-1 mutant and tt19-2 mutant) were observed visually. With respect to vegetative parts, purple pigmentation derived from anthocyanins was not visually observed at the basal region of the stem in tt19 (FIGS. 2A, B).

Subsequently, the anthocyanin content in the two tt19 mutants was assessed. Rosette leaves (100 mg) were harvested from about 45-days-old plants of Col ecotype, tt19-1 mutant, tt19-2 mutant and tt4 mutant grown in a growth cabinet controlled at 23° C. with 16 h-light period. They were ground under liquid nitrogen, and mixed with 5 ml of 1% HCl/methanol. After two-nights extraction at 25° C. with gentle suspension under dark condition, Folch partition was performed and $OD_{300-700}$ for the upper phase was measured using spectrophotometer (DU530, Beckman, USA). The average values were obtained from 5 independent experiments, except for tt4 mutant in duplicate.

In the wild type Columbia (Col) ecotype a sharp peak of absorbance at around 530 nm was remarkable, whereas a great reduction of the corresponding peak was observed in both tt19 mutants. The average $OD_{530}$ values were 0.091±0.011, 0.041±0.009, 0.038±0.004, and 0.008±0.001 in Col ecotype, tt19-1 mutant, tt19-2 mutant, and tt4 mutant, respectively. Anthocyanin accumulation in tt19 mutants was somewhat enhanced by cultivation under the strong light conditions such as that in a greenhouse (data not shown).

Figure 2:
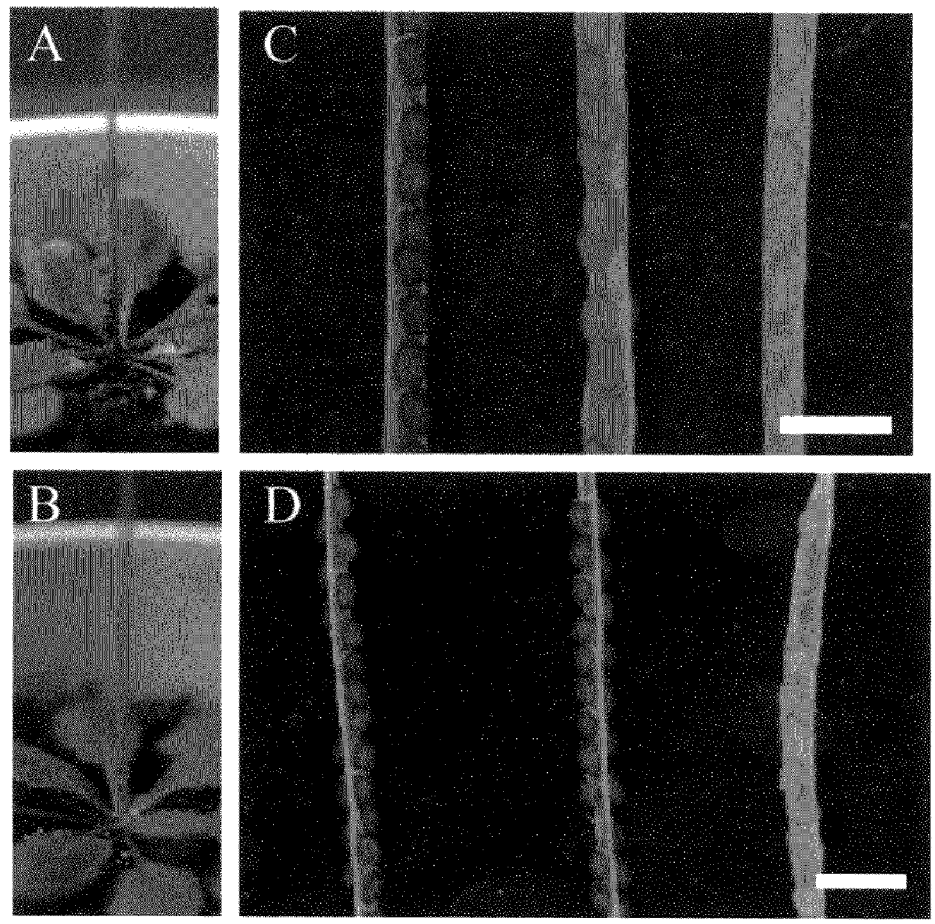
FIG. 2 is phenotypic characterization of tt19 mutants; (A) and (B) show accumulation of flavonoid pigments at the base of the stem in Col ecotype (A) and tt19-1 mutant (B) grown for 1 month in a growth chamber; (C) shows mature siliques at the ripening stage of Col ecotype (left), tt19-1 mutant (center), and tt4 mutant (right); (D) shows siliques desiccated further 7 weeks from the ripening stage (C); scale bars indicate 1 mm.

Seed coat of tt19 mutants displayed pale-brown color at the ripening stage, in contrast to brown in Col ecotype and yellow in tt4 mutant (FIG. 2C). However, browning of the testa of the tt19 mutants proceeded according as the desiccation period prolonged. Seed coat of tt19 has eventually darkened as much as that of Col ecotype after the long-term desiccation (FIG. 2D). Other phenotypic traits seemed normal in tt19 mutants.

Example 3

Naringenin Feeding

In this example, the effect of naringenin on anthocyanin pigmentation in Arabidopsis seedlings was investigated.

It is known that sugars induce anthocyanin pigmentation in Arabidopsis seedlings (Tsukaya, H. et al., (1991) Plant Physiol. 97, 1414-1421). Before naringenin feeding experiment, proper concentration of sucrose for the induction of anthocyanin accumulation was determined.

Surfaces of dried seeds of Col ecotype were sterilized by treatment with 70% EtOH for 1 minute, then with sodium hypochlorite solution with 0.05% Tween-20 (ca. 0.3% active chlorine) for 10 minutes, and rinsed five times in sterilized distilled water. The seeds were sown on MS/sucrose/agar (0.8%) plates containing sucrose at a concentration of 0, 1, 2, 5, 10 or 20%. After vernalization at 4° C. for 5 days, the plates were incubated in a growth chamber set at 23° C. with continuous light and were observed everyday by a stereomicroscope (Stemi SV11, Zeiss, Germany). The results are shown in FIG. 3A.

In Col ecotype seedlings, the more the sucrose concentration increased to 5%, the more marked was the progress of anthocyanin pigmentation at upper hypocotyls and abaxial and marginal regions of cotyledons (FIG. 3A). Ten percent of sucrose provoked delay of development and twenty percent caused inhibition of germination in Col ecotype (data not shown). Two tt19 mutant lines also showed retardation of the germination and seedling development on the plates in the presence of more than 10% sucrose. Therefore, 5% sucrose was thought to be the best in this experiment.

Figure 3:
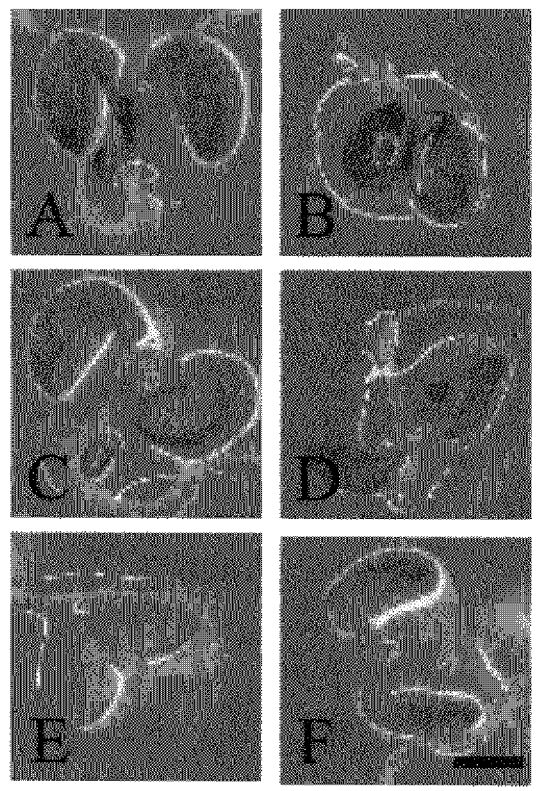
FIG. 3 shows Arabidopsis seedlings grown in MS/sucrose/agar plates with or without 0.1 mM naringenin; (A) and (B) are Col ecotype; (C) and (D) are tt19-1 mutant; (E) and (F) are tt4 mutant. (A), (C) and (E) were grown without naringenin, whereas (B), (D) and (F) were grown with naringenin; all seedlings were grown at 23° C. under continuous light for 5 days; scale bar represents 1 mm.

Surfaces of dried seeds of Col ecotype, tt19-1 mutant, tt19-2 mutant and tt4 mutant were sterilized by treatment with 70% EtOH for 1 minute, then with sodium hypochlorite solution with 0.05% Tween-20 (ca. 0.3% active chlorine) for 10 minutes, and rinsed five times in sterilized distilled water. The seeds were sown on MS/sucrose/agar (0.8%) plates (with sucrose at a concentration of 5%) containing 0.1 mM naringenin (Shirley, B. W. et al., (1995) Plant J. 8, 659-671) or naringenin-free plates (with sucrose at a concentration of 5%). As described by Noh and Spalding (Noh, B. and Spalding, E. P. (1998) Plant Physiol. 116, 503-509), naringenin (SIGMA) dissolved in 50% EtOH was added to an autoclaved MS medium. After vernalization at 4° C. for 5 days, the plates were incubated in a growth chamber set at 23° C. with continuous light and were observed everyday by a stereoscopic microscope (Stemi SV11, Zeiss, Germany). The results are shown in FIG. 3.

In Col ecotype seedlings, addition of naringenin reinforced anthocyanin pigmentation to some extent (FIG. 3B). Although some effects were observed in seedling development on the 5% sucrose media, tt4 mutant exhibited anthocyanin pigmentation accumulation by naringenin feeding (FIG. 3F), as reported previously (Kubasek, W. L. et al., (1992) Plant Cell 4, 1229-1236). On the other hand, tt19 mutants showed no accumulation of anthocyanins despite the naringenin feeding (FIG. 3D). These results indicate that the TT19 gene functions in the downstream step from F3H reaction in anthocyanin biosynthetic pathway (see FIG. 1).

Example 4

Vanillin Treatment

In general, brown color of Arabidopsis wild type testa is mainly contributed by oxidation of PAs (Chapple, C. C. S. et al. (1994) Secondary metabolism in Arabidopsis. In Arabidopsis (Meyerowitz, E. M. and Somerville, C. R. eds). New York: Cold Spring Harbor Laboratory Press, pp. 989-1030). Vanillin reacts with monomer units of PA precursors and terminal units of PAs under acidic conditions, resulting in the deposition of red pigments in their accumulated sites (Deshpande, S. S. et al., (1986) Crit. Rev. Food Sci. Nutr. 24, 401-449). In Example 4, in order to determine the presence and/or distribution of these PA precursors, vanillin treatment was carried out in immature tt19 seeds.

Figure 4:
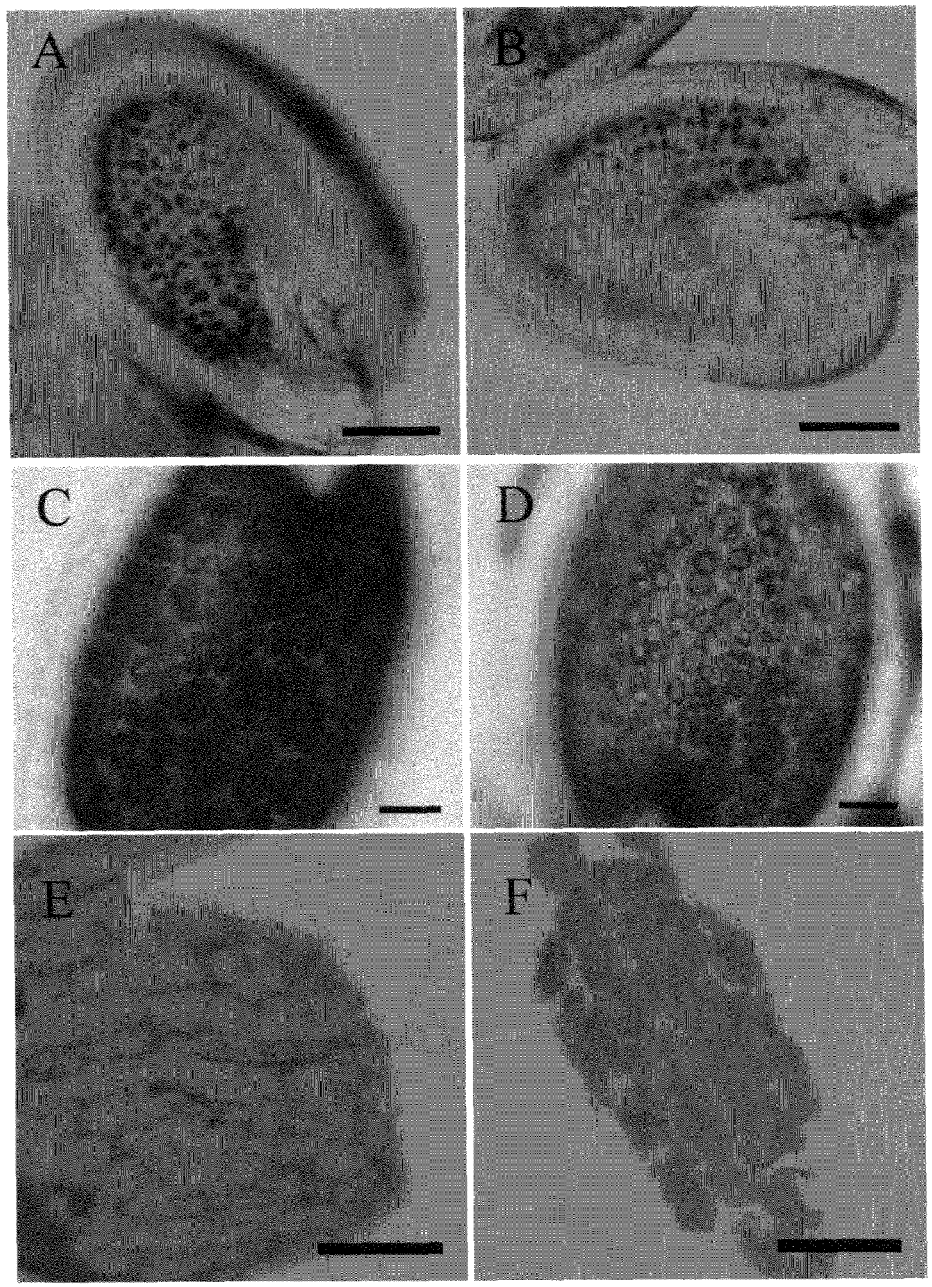
FIG. 4 shows depositional patterns of PA precursors in seed coat of Col ecotype ([A], [C], and [E]) and tt19-1 mutant ([B], [D], and [F]); (A) and (B) are Day 1 After Flowering (DAF) immature seeds; (C) and (D) are DAF5 immature seeds; (E) and (F) are DAF17 seed coat segments; scale bars indicate 50 µm.

Vanillin treatment was performed essentially according to the method of Debeaujon et al. (2000). Samples up to DAF10 were investigated by whole-mount observation. After DAF10, dissection of seed coat segments from vanillin-treated seeds was performed, and the endothelium layers were observed using microscope (Axioskop, Zeiss, Germany). The results are shown in FIG. 4.

At Day 1 After Flowering (DAF1), red coloration was recognized in both Col ecotype and tt19 mutants and no remarkable difference was observed between the two (FIGS. 4A, B). However, posterior to around DAF3, depositional patterns of red pigments were obviously different between Col ecotype and tt19 mutants seeds (FIGS. 4C-F). The most conspicuous difference was observed at DAF5 (FIGS. 4C, D). That is, in testa of Col ecotype, it appeared that red pigments were accumulated in large central vacuoles, each of which seemed fully expanded within a cell of an endothelium layer of the testa (FIG. 4C).

On the other hand, although red pigments were unequivocally detected in the testa of the tt19 mutants, their spatial occurrence was more restricted than that in Col ecotype, and red pigments were accumulated in a few smaller vacuoles within each of the cells of an endothelium layer (FIG. 4D). Difference in distribution of red pigments was continuously detected until DAF9-10, after which whole-mount observation was difficult probably due to hardening of the seed coat. In order to examine the distribution of PA precursors in such a hardened seed coat, the present inventors tried to dissect seed coat segments and their innermost (endothelium) layer was observed. Examples at DAF17 are shown in FIGS. 4E and 4F. In Col ecotype, red pigmentation was very weak and marginal on their constitutive cells (FIG. 4E). In contrast, red pigments completely filled the interior of each of the endothelium cells in tt19 mutants (FIG. 4F).

Example 5

Molecular Mapping of the TT19 Gene

Using F2 individuals derived from crosses of ecotype Landsberg erecta (Ler) ecotype to tt19-1 mutant or tt19-2 mutant, molecular mapping of TT19 gene was carried out.

Specifically, if F2 individuals are obtained by crossing ecotype Ler ecotype with tt19-1 mutant or tt19-2 mutant having the background of Col, the ratio of Col type to Ler type for a single marker is ideally close to 1:1. However, if these F2 individuals are selected using the phenotype of tt19 mutation as a marker, the ratio of Col type to Ler type will increase as the locus of TT19 gene is progressively approached on the genome since the marker is invariably of the Col type. This propensity was used to gradually specify candidate regions for the locus of TT19 gene.

Forty-five and 103 F2 plants showing tt phenotype were obtained from crosses of Ler ecotype with tt19-1 mutant and tt19-2 mutant, respectively. Genomic DNA was extracted from rosette leaves by using DNeasy Plant Mini Kit (Qiagen) according to the manufacturer's instructions. Molecular mapping was progressed using their F2 genomic DNA in relation to the linkage with the CAPS and SSLP markers according to the standard methods (Bell, C. J. and Ecker, J. R. (1994) Genomics 19, 137-144).

For tt19-1 mutated allele, DNA markers on 20.6, 23.7, and 25.3 cM of chromosome 5 on RI map showed gradual reduction of recombination frequencies, and TT19 gene was localized around 29.5 cM. On the other hand, recombination values on 42.2 and 50.5 cM markers showed localization of TT19 gene around 35.5 cM. In addition, recombination was never detected among 45 F2 individuals over the region between those two possible locations for TT19 gene. This phenomenon is often found in mutants induced by ion beams, and leads to an assumption that inversion has taken place in this region with the breakpoints around 29.5 and 35.5 cM in tt19-1 mutant.

Then, mapping of tt19-2 mutated allele was performed. For tt19-2 mutated allele, gradual decline of recombination values into a chromosomal site around 35 cM was obtained among 103 F2 individuals. These results allowed the present inventors to infer that TT19 gene was located in the vicinity of 35 cM region and, in tt19-1 mutant, one of the breakpoints of the putative large inversion coincided with the TT19 locus.

Based on the inference mentioned above, the present inventors firstly focused annotations on five BAC or P1 clones, to which map position of tt19-2 mutated allele has been restricted. Because primary characteristic for tt19 mutants is a lack or reduced-level of anthocyanins, TT19 gene would be involved in synthesis and/or accumulation of anthocyanins. Indeed, several TT19 candidates could be found on the restricted five BAC or P1 clones.

Then, on the basis of mapping data from tt19-2 mutated allele, the present inventors started to analyze the most probable candidate, annotated as a glutathione S-transferase (GST)—like gene on P1 clone MKP11.

Four primer sets covering the overall region of the GST-like gene which was the most probable candidate for TT19 gene were designed in the vicinity of the putative TT19 locus:

TT19-f0 (5'-GAG AAC CCC AAA AAC GTC AC-3'; SEQ ID NO:3) and

TT19-r0 (5'-GTT GTG AGG GTT GGG TAG AA-3'; SEQ ID NO:4);

TT19-f1 (5'-GTG GTT GTT GGG AAG AGA AG-3'; SEQ ID NO:5) and

TT19-r1 (5'-CGA TGG CTC GTG ATT CTT AG-3'; SEQ ID NO:6);

TT19-f2 (5'-GGT CAA GTT CCA GCC ATA GA-3'; SEQ ID NO:7) and

TT19-r2 (5'-AGC GAG AGG AAA GTG GAA CA-3'; SEQ ID NO:8); and

TT19-f3 (5'-CCC TCA TTA GGC CAA GAG AA-3'; SEQ ID NO:9) and

TT19-r3 (5'-GAG CTT ATG TGG GGA AAG TC-3'; SEQ ID NO:10).

These primers were so set that no amplification could occur when the GST-like gene was destroyed in relation to the genomic DNA of two tt19 mutants whereas amplification was possible when the gene was not destroyed.

Using these primer combinations, PCR amplification was carried out under the program consisting of the first denaturation step of 95° C. for 10 min; 40 cycles of a sequence consisting of 94° C. for 0.5 min, 57° C. for 0.5 min, and 72° C. for 1 min; and the final extension step of 72° C. for 7 min. Amplified fragments were separated in 1.5% agarose gel electrophoresis. As a result, two out of four fragments were not amplified in tt19-1 mutant, suggesting that there was a breakpoint of the inferable large inversion in these non-amplified DNA regions of tt19-1 mutant.

Example 6

Molecular Cloning of TT19 Gene

In this example, molecular cloning of TT19 gene was performed by recovery, purification, and sequencing of the amplified fragments.

In order to isolate DNA fragment including the rearranged point in two tt19 mutant loci, thermal asymmetric interlaced (TAIL)-PCR was carried out (Liu, Y.-G. and Whittier, R. F. (1995) Genomics 25, 674-681).

Two sets of three nested specific primers, one set consisting of MKP11-R4, 5'-ATC AAG TAC CCC ATC GCC GGC ATG T-3' (SEQ ID NO:11); MKP11-R5, 5'-GGC ATG TGC GTC AAA TCA GCC ATA G-3' (SEQ ID NO:12) and MKP11-R6, 5'-AAC CGG TTC GAA GAA AGC CGG TTA T-3' (SEQ ID NO:13), and the other set consisting of MKP11-F7, 5'-ATA TGG ACA GGT AAC AGC AGC TTG TC-3' (SEQ ID NO:14); MKP11-F8, 5'-GCA GCT TGT CCA CAA AGA GTC TTG CT-3' (SEQ ID NO:15) and MKP11-F9, 5'-GCT TTG TTT TCT CGA GAA AGG AAT TG-3' (SEQ ID NO:16), were used respectively for isolation of two junction sequences of inverted DNA in tt19-1 mutant locus.

Three oligonucleotides; bCC5-8-R1 (5'-GAC GTC ACA TTT CTC GCC TAA CCT-3'; SEQ ID NO:17), bCC5-8-R2 (5'-GAG GGG TTG GGC CAG AAC GTT GAA-3'; SEQ ID NO:18), and bCC5-8-R3 (5'-CGA TGG CTC GGT GCT CTA GAG ACT-3'; SEQ ID NO:19) were used as the nested specific primers in tt19-2 mutant locus.

Two arbitrary degenerated primers [AD2 (5'-NGT CGA SWG ANA WGA A-3'; SEQ ID NO:20) and AD3 (5'-WGT GNA GWA NCA NAG A-3'; SEQ ID NO:21)] were synthesized according to the sequences described by Lie et al. (Liu, Y.-G. et al., (1995a) Plant J. 8, 457-463). The sequence of another AD primer (AD1) was 5'-GTN CGA SWC ANA WGT T-3' (SEQ ID NO:22). In those sequences, S means G or C, W means A or T, and N refers to either one of the bases.

Using the nested specific primer sets and the given AD primer, TAIL-PCR cycling was run in eppendorf Mastercycler gradient (Eppendorf) according to the methods of Liu et al. (1995a, supra), except that the annealing temperature in 5 high stringency cycles was 65° C. and that the duration of each extension step was changed from 2.5 min to 3 min. The PCR products were fractionated, purified, and sequenced as described above.

Figure 5:
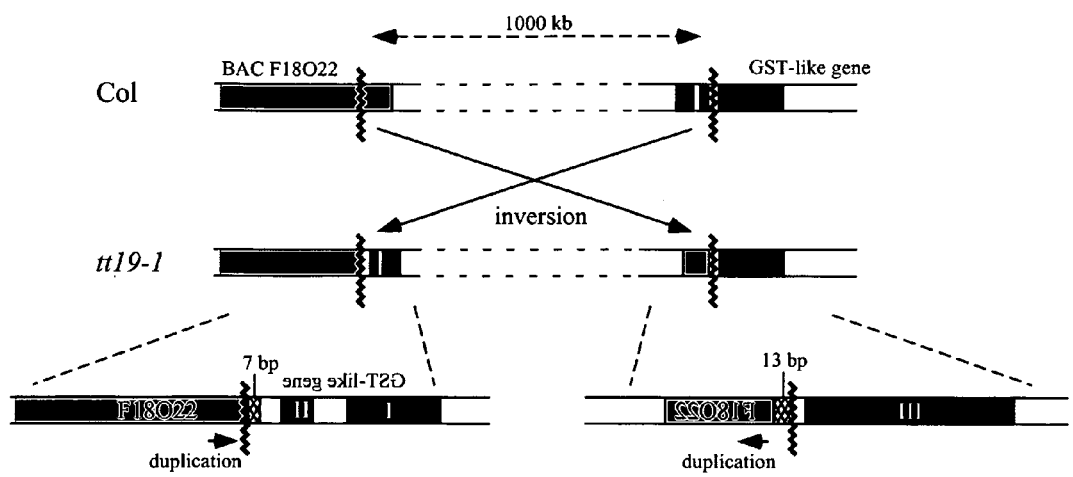
FIG. 5 is a schematic representation of mutated loci in two tt19 mutants; (A) shows structural alteration in tt19-1 mutant; large inversion involving GST-like locus had taken place; exons of GST-like gene are shown as black boxes; chromosomal regions of BAC F18022 are represented as gray; filler DNA regions are shown as hatched boxes; it should be noted that 6 bp fragment (corresponding to 98506-11 nt in F18022) was duplicated at both boundaries of the inverted fragment, and shown as black arrows; (B) shows mutation in GST-like locus in tt19-2 mutant; exons are shown as black boxes; gray arrow indicates a transcription initiation site; each number represents nt position in BAC MKP11; a part of the fragment within 743-17466 nt in MKP11 was detected in the genome of the tt19-2 mutant by PCR and sequence analyses, but translocated position is unclear.
Figure 5:
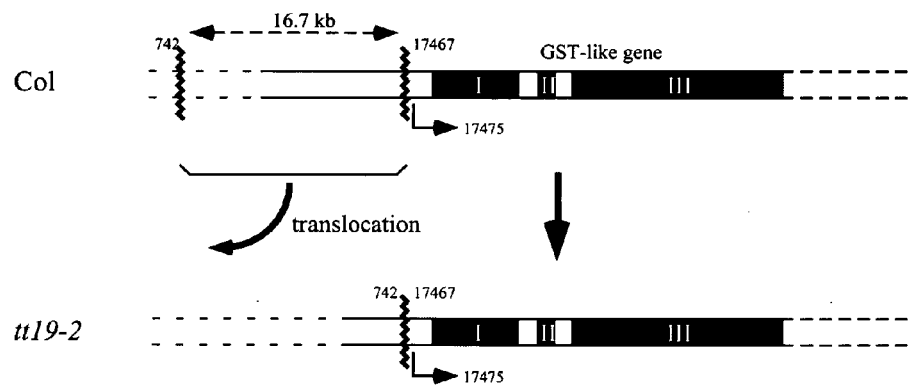

Sequencing of the TAIL-PCR product obtained demonstrated that the downstream region of the GST-like gene was joined to the sequences completely homologous to those of BAC F18022 on chromosome 5 in the reverse direction, with the filler-DNA-like 13 bp sequence at the border (FIG. 5A). Origin of the filler-DNA-like sequence (13 bp) was not clarified because of dispersion of identical sequence throughout Arabidopsis genome. The other rejoining point of the inversion was also determined by TAIL-PCR and sequencing, and a fragment containing F18022 and MKP11 sequences was detected, again with the filler-DNA-like segment of 7 bp at the border (FIG. 5A).

Therefore, the present inventors concluded that in tt19-1 mutant, inversion had occurred with the breakpoints on F18022 and the second intron of GST-like gene on MKP11. The size of this inversion was estimated as about 1000 kb in length based on Arabidopsis genome database. Annotation published by TAIR indicates that there is no gene at the breakpoint on BAC F18022. In addition, it was shown that 6 bp fragment (TAGAAA) in F18022 was duplicated with inverted direction at both borders of the inversion.

PCR analysis was also carried out for the GST-like locus in tt19-2 mutant. When using f1 and r1 primers, amplification was not observed, indicating that tt19-2 mutant might have undergone DNA rearrangement with a breakpoint on the f1-r1 region. TAIL-PCR revealed that the −53 nucleotide was rejoined with region further 16.7 kb upstream when the translation initiation site was defined as +1 (FIG. 5B). Sequence analysis did not find any other mutation on the GST-like gene from the rejoined site to 60 bp downstream of the exon 3. A part of DNA region deleted from the GST-like locus was amplified by PCR in the genome of the tt19-2 mutant, and their sequences were completely identical to those of the wild type.

Therefore, the fragment of 16.7 kb in length seems to be translocated into the other genomic region of the tt19-2 mutant, although translocated site was not detected in the present study. As in the case of tt19-1 mutant, Arabidopsis annotation indicates that there is no gene on the upper breakpoint of 16.7 kb fragment of the tt19-2 mutated allele.

Example 7

Phylogenetic Analysis

Figure 6:
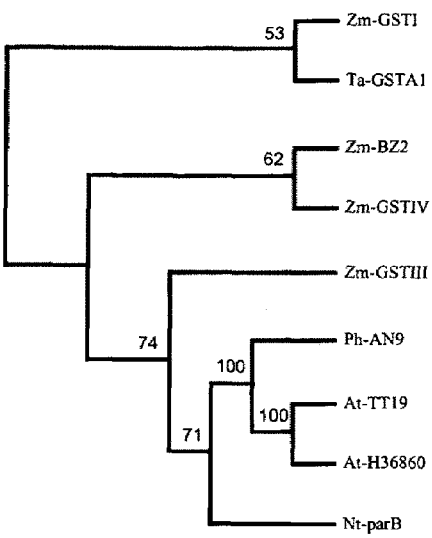
FIG. 6 shows the protein sequence of TT19 and phylogenetic tree; (A) depicts multiple alignment of the deduced amino acid sequences of TT19 (At-TT19) (SEQ ID NO: 2), Arabidopsis EST H36860 (At-H36860) (SEQ ID NO: 39), petunia AN9 (Ph-AN9) (SEQ ID NO: 40), tobacco parB (Nt-parB) (SEQ ID NO: 41), maize GSTI, GSTIII, GSTIV, and BZ2 (Zm-GSTI, Zm-GSTIII, Zm-GSTIV, and Zm-BZ2) (SEQ ID NOS 42-44 and 46, respectively), and wheat GSTA1 (Ta-GSTA1) (SEQ ID NO: 45); all references for these GSTs are included in Alfenito et al. (1998, supra); sites of identical amino acids are indicated as asterisks; (B) depicts phylogenetic tree among GST proteins shown in (A); an unrooted consensus tree was obtained by the neighbor-joining method; bootstrap values are indicated at each branch.
Figure 7:
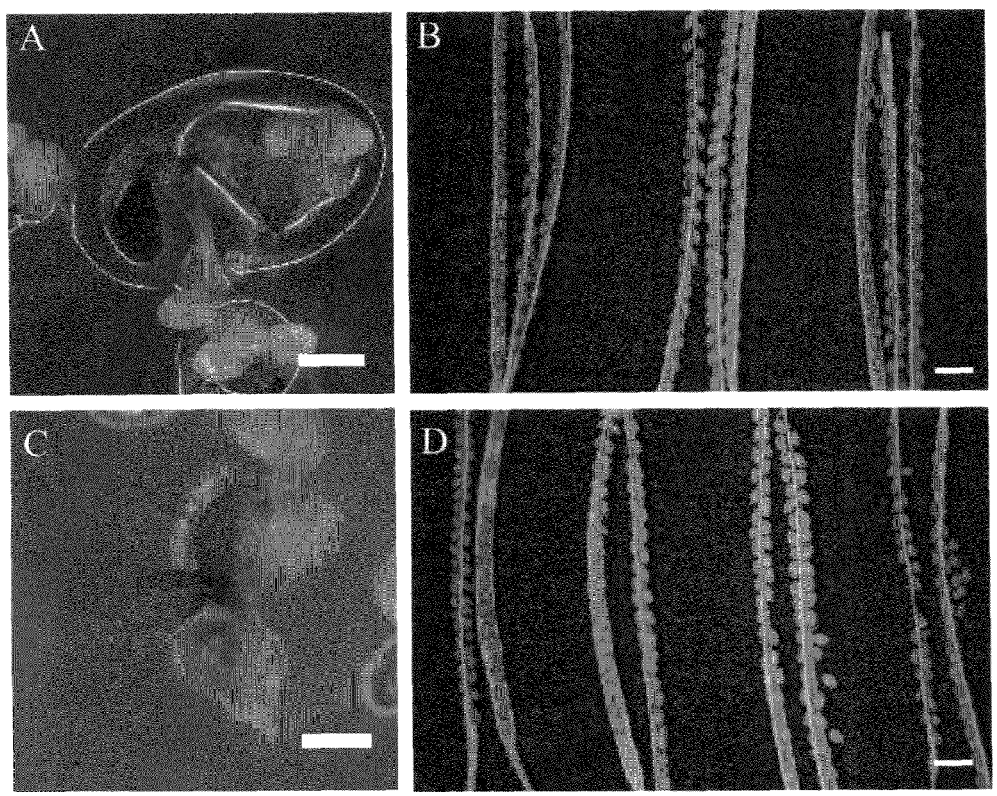
FIG. 7 shows functional complementation of tt19 mutants by the wild type TT19 gene with its authentic promoter ([A] and [B]) or by the petunia AN9 gene driven by CaMV 35S promoter ([C] and [D]); (A) and (C) are T1 seedlings with anthocyanin pigmentation; (B) and (D) show seed color at the ripening stage; from left to right: Col ecotype, tt19 mutant, and T1 siliques; as a positive control, T1 siliques with 35S: TT19 construct are placed at the right end of (D); scale bars indicate 1 mm.

Because both of tt19 mutants (i.e. tt19-1 mutant and tt19-2 mutant) held mutations in the GST-like gene, the present inventors predicted it as TT19 gene. In order to verify this prediction, the present inventors performed multiple alignment using Clustal W ver. 1.7 (Thompson, J. D. et al., (1994), supra). They also performed the neighbour-joining method (Saitou, N. and Nei, M. (1987) Mol. Biol. Evol., 4, 406-425) using PHYLIP ver. 3.57 (Felsenstein, J. (1995) PHYLIP (Phylogeny inference package) version 3.57c. University of Washington Press, Seatlle). The results are shown in FIGS. 6 and 7.

The deduced amino acid sequence of the wild type TT19 gene shows high identity of about 70% to that of an Arabidopsis EST clone H36860 and about 50% to that of a petunia GST gene, AN9 (FIG. 6A). Phylogenetic analysis using several plant GSTs indicated that TT19 primarily clustered with H36860, then with AN9 (FIG. 6B).

Example 8

Functional Analysis of the Wild-type TT19 Gene

In this example, the wild-type TT19 gene was introduced into tt19 mutants in order to see if the phenotype of the mutants would restore to the wild type.

Wild-type TT19 gene was isolated from P1 clone MKP11 (Liu, Y.-G. et al., (1995b) Plant J. 7, 351-358). KpnI-SacI genomic fragment (ca. 2.4 kb) including the wild type TT19 gene and its authentic promoter was fractionated and recovered from agarose gel as described above and subcloned in pUC19 digested with the same enzyme. After sequencing the boundary between the vector arm and the insert, the genomic TT19 gene was isolated and introduced into binary vector pBI101 (Jefferson, R. A. et al., (1987) EMBO J. 6, 3901-3907).

After confirming the sequence of the insert including the boundary region, the binary vector was transformed into Agrobacterium GV3101 by electroporation. The Agrobacterium clones having the binary vector were infected to the tt19 mutants by the floral dip method (Clough and Bent, 1998, supra) so as to obtain T1 seedlings. After screening the T1 seeds using kanamycin (50 mg/l) and Claforan (166 mg/l), the transformants were grown and their phenotype was examined primarily in association with the deposition of flavonoid pigments.

All of the five independent T1 plants (named as tt19/AU: TT19 line) derived from either of tt19 mutant lines restored anthocyanin accumulation in seedlings (FIG. 7A) and brown pigmentation in testa at the ripening stage to the wild type level (FIG. 7B). This is the conclusive evidence that disruption of TT19 gene was responsible for the flavonoid deficient phenotype of tt19 mutants.

Example 9

Expression of TT19 and Other Flavonoid Genes

In this example, firstly, cDNA clones corresponding to TT19 gene was searched in GenBank database. One clone 169M6 with very high identity to the mRNA was found. Sequencing of this cDNA clone uncovered that it consisted of completely identical sequences to the coding region of TT19 gene, with a 45 bp of 5' non-translated region, a 272 bp of 3' non-translated region and a poly-A tail (this coding region is herein designated as SEQ ID NO:1). Based on this result, it was conceivable that 169M6 was derived from the transcription of TT19 gene. Moreover, it was shown that a breakpoint in tt19-2 mutated allele was localized at 9 bp upstream from the putative transcription initiation site (FIG. 5B).

In order to determine whether TT19 gene is expressed in two tt19 mutants, reverse transcription (RT)-PCR was carried out using total RNA from rosette leaves grown in a greenhouse for 6 weeks.

First, using RNeasy Plant Mini Kit (Qiagen), total RNA was extracted from various tissues of 6-week old plants grown in a greenhouse. Contamination of genomic DNA was prevented by using an RNase-free Dnase set (Qiagen) in accordance with the manufacturer's protocol. For RNA preparation from seedlings and roots, seedlings were grown vertically on MS/sucrose (1%)/agar (0.8%) plates for 5 and 10 days, respectively, in a 23° C. incubator with continuous light, and RNA extraction was performed as described above.

Then, expression of TT19 and other flavonoid genes was determined by RT-PCR. Using 500 ng of total RNA, RT-PCR was performed with Takara RNA LA PCR Kit (ver. 1.1, Takara) employed in accordance with the manufacturer's protocol. The PCR program consisted of the first denaturation step at 95° C.×2 min, followed by 30 cycles of a sequence consisting of denaturation at 94° C.×0.5 min, annealing at 57° C.×0.5 min and extension at 72° C.×1.5 min, and the final extension step at 72° C.×7 min. The hot start strategy was performed in all RT-PCR reactions.

For TT19 expression, TT19-RT/f2 (5'-GAA CAT CTT CTT CGT CAG CCA TTT GGT CAA-3': SEQ ID NO:23) and TT19-RT/r1 (5'-GGT TCT TCA GAT CAT CAT AAA TTG GAG CTA-3': SEQ ID NO: 24) were used as specific primers. Using the primer pair reported by Nesi et al. (Nesi, N., et al., (2000) Plant Cell 12, 1863-1878), expression of elongation factor 1αA4 (EF1αA4) was determined as an internal control. The obtained PCR products were respectively 548 bp and 709 bp in size.

For chalcone synthase (CHS), flavonoid 3'-hydroxylase (F3'H) and dihydroflavonol 4-reductase (DFR), the primers employed were identical to those reported by Nesi et al. (2000, supra; N. et al., (2001), Plant Cell 13, 2099-2114) except for the DFR-reverse primer. The following primers were specifically employed:

for CHS, CHS-UP; 5'-ATG GCT GGT GCT TCT TCT TTG G-3' (SEQ ID NO: 25) and CHS-RP; 5'-TCT CTC CGA CAG ATG TGT CAG G-3' (SEQ ID NO: 26);

for F3'H, F3'H-UP; 5'-CAT GGC AAC TCT ATT TCT CAC-3' (SEQ ID NO: 27) and F3'H-RP; 5'-CGT CAC CGT CAA GAT CAG TTC C-3') (SEQ ID NO:28); and for DFR, DFR-UP; 5'-ATG GTT AGT CAG AAA GAG ACC G-3' (SEQ ID NO: 29) and DFR-RT/r1; 5'-GAC ACG AAA TAC ATC CAT CCT G-3' (SEQ ID NO: 30).

The obtained PCR products were respectively 712 bp, 851 bp and 497 bp in size.

As for the expression of chalcone isomerase (CHI), flavanone 3-hydroxylase (F3H) and leucoanthocyanidin dioxygenase (LDOX), specific primers were designed as follows:

for CHI, CHI-f1 (5'-CTC AAC AAT GTC TTC ATC CAA CGC CT-3'; SEQ ID NO: 31) and CHI-r1 (5'-CGA AAA CGC AAC CGT AAG AGA G-3'; SEQ ID NO: 32);

for F3H, F3H-f1 (5'-GCC GGA GAG TCT AAG CTC AAC T-3'; SEQ ID NO: 33) and F3H-r1 (5'-CCA CGG CCT GAT GAT CAG CAT T-3'; SEQ ID NO: 34); and for LDOX, LDOX-f2 (5'-GAT GGT TGC GGT TGA AAG AGT T-3'; SEQ ID NO: 35) and LDOX-r2 (5'-AAA GCG CTT ACA TCG GTG TGA G-3'; SEQ ID NO: 36).

The obtained PCR products were respectively 535 bp, 808 bp and 714 bp in size.

Figure 8:
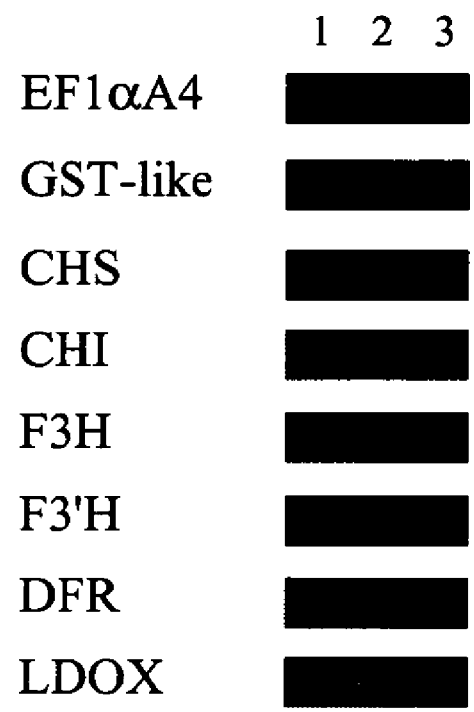
FIG. 8 shows RT-PCR for flavonoid structural genes in Col ecotype (lane 1), tt19-1 mutant (lane 2), and tt19-2 mutant (lane 3); EF1αA4 is elongation factor 1αA4; other abbreviations are included in FIG. 1.

As expected, a single band was amplified in Col RNA, whereas no band was detected in RNA samples from either of the two tt19 mutants (FIG. 8). Therefore, it was demonstrated that expression of TT19 gene was abolished in two tt19 mutants.

Expression pattern of TT19 gene in various organs of Col plants was also examined. Expression of TT19 gene was detected in all organs tested, including seedlings, roots, stems, leaves, floral buds, flowers, and developing siliques (data not shown), indicating that TT19 gene is constitutively expressed at the whole plant level. In addition, RT-PCR also revealed that disruption of the TT19 gene expression did not affect expression of other flavonoid structural genes such as CHS, CHI, F3H, F3'H, DFR, and LDOX (FIG. 8).

Example 10 tt19 Ban Double Mutant Analysis

In this example, double mutants of tt19 gene and BANYULS (BAN) (Albert, S. et al., (1997) Plant J. 11, 289-299) were created and analyzed in order to reveal the mechanism behind the action of TT19 gene.

BANYULS (BAN) encodes one of the enzymes involved specifically in PA biosynthetic pathway in Arabidopsis (Xie et al., 2003, supra; see FIG. 1), and loss-of-function mutation in the BAN gene resulted in no flavan 3-ols in the seed coat (Devic, M. et al., (1999) Plant J. 19, 387-398). The preliminary experiment showed that anthocyanin spotted testa (ast) mutant (Tanaka et al., 1997b, supra) was not complemented by ban mutant, indicating that ast was allelic to ban (Winkel-Shirley, 2001, supra), and caused deletion of 49 bp (+114~162 nt) in BAN, resulting in a null mutant. Therefore, ast is hereunder referred to as ban-4. To investigate interaction between tt19 and ban, double mutant with either of tt19 alleles and ban-4 was constructed and its phenotype was characterized.

The tt19 ban double mutants were created in the following manner. First, tt19 mutant was crossed with ban mutant to create F1 individuals. The F1 individuals are characterized in that all of them are hetero for both the tt19 and ban loci. By inbreeding the F1 individuals, F2 individuals were created and from them, tt19 ban double mutants whose theoretical frequency was 6.25% were selected on the basis of the nucleotide sequences of TT19 and BAN.

Figure 9:
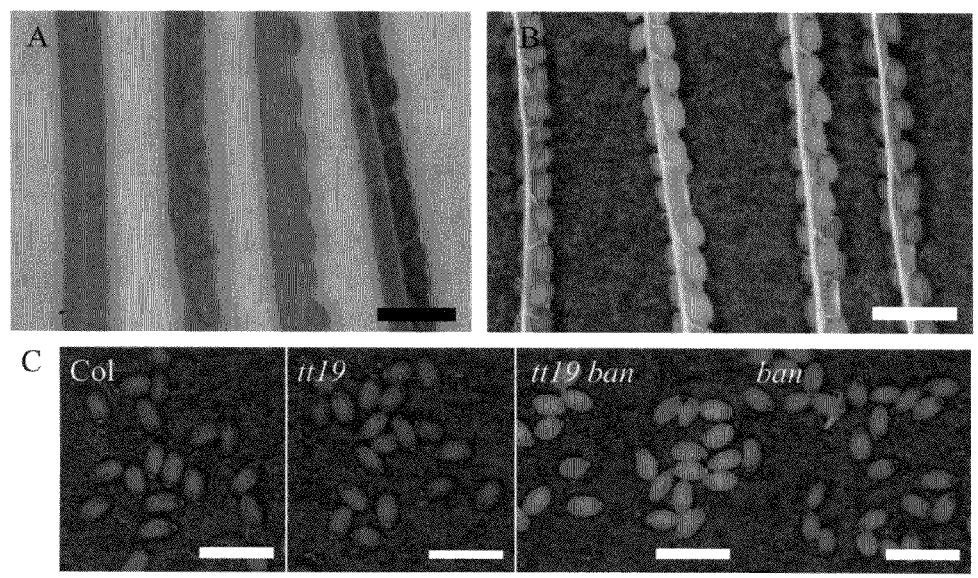
FIG. 9 shows testa phenotype of tt19 ban double mutants; (A) depicts DAF8 immature siliques; from left to right: Col ecotype, tt19 mutant, tt19 ban double mutant, and ban mutant; (B) depicts DAF20 mature siliques; from left to right: Col ecotype, tt19 mutant, tt19 ban double mutant, and ban mutant; (C) depicts seed color after additional 7-week desiccation from the ripening stage; from left to right: Col ecotype, tt19 mutant, tt19 ban double mutant, and ban mutant; scale bars represent 1 mm.
Figure 10:
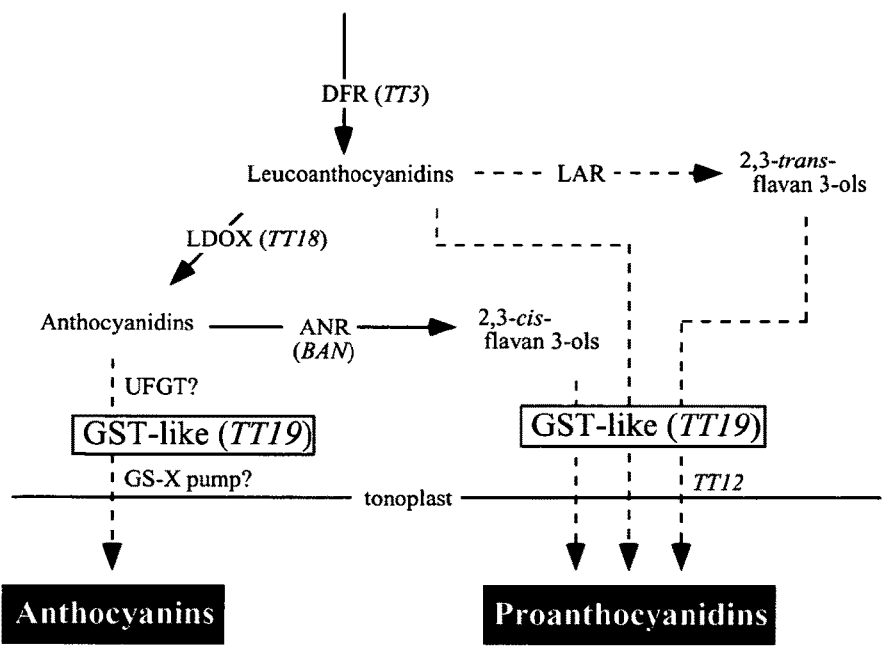
FIG. 10 shows flavonoid late biosynthetic pathway and their accumulation in Arabidopsis; UFGT, UDP-glucose:flavonoid glucosyltransferase; GST-like, glutathione S-transferase-like; GS-X pump, glutathione-specific pump; other abbreviations are included in FIG. 1.

Pigmentation of anthocyanins was not observed in leaves and stems of tt19 ban double mutant. In immature seed coat of the double mutant conspicuous and precocious accumulation of anthocyanins was not observed, although very leaky coloration was recognized (FIG. 9A). These results indicate that tt19 was epistatic to ban for the anthocyanin accumulation at the whole plant level. Vanillin assay revealed that PA precursors were never detected in immature seed coat of the double mutant, like in that of ban (Devic et al., 1999, supra) and ban-4 used herein (data not shown). For seed color at the ripening stage, ban showed grayish dull brown, tt19 pale-brown, and double mutant pale-brown with subtle gray (FIG. 9B). One of the characteristics of tt19, which caused darkening of the seed color during after-ripening (FIG. 2D), was obviously lacking and no change in seed color was observed in the double mutant after the additional desiccation period (FIG. 9C).

Example 11

Functional Complementation of tt19 Mutation with Petunia AN9

In order to determine the function of TT19, petunia AN9, a putative homolog of TT19, was driven under CaMV 35S promoter, and this construct was introduced into tt19 mutants to investigate whether the deficiency of pigmentation in the tt19 mutants could be complemented by the AN9 gene which is a homolog in petunia.

The petunia (V26 line) AN9 cDNA was amplified from total RNA of floral buds by the RT-PCR mentioned above. In order to amplify petunia AN9, AN9-5' (5'-GGA TCC ATG GTT GTG AAA GTG CAT GG-3'; SEQ ID NO: 37) and AN9-3' (5'-GAG CTC GTC CCG TAC TCC ACA ACA AT-3'; SEQ ID NO: 38) were used as primers. RT-PCR was performed as in Example 9, except for annealing temperature of 55° C. By sequencing the TA-cloning products, nucleotide exchange was found in exon 3 in all AN9 cDNA clones, leading to one amino acid exchange from the published sequence ($Val^{80} \rightarrow Asp^{80}$).

Then, as described in Example 8, plasmids were digested with BamHI and SacI, and inserts were also subcloned into pUC19. For control experiment, the inserts of EST clone 169M6 were recovered by digestion with SalI and NotI, ligated with two specific adaptors including BamHI- and SacI-recognition sites, respectively, and subcloned into pUC19. After sequencing the boundaries between vector arms and inserts, two kinds of cDNA (TT19 cDNA and AN9 cDNA) were isolated and introduced into binary vectors pBI101 and pBI121, respectively, (Jefferson, R. A. et al., (1987), supra) to perform complementation analysis. After ascertaining the sequences of the inserts including the boundary regions, two kinds of binary vectors were distinctly transformed into Agrobacterium GV3101 by electroporation. Agrobacterium clones possessing the binary vectors were infected to tt19 mutants by the floral dip method (Clough and Bent, 1998, supra), and the resulting T1 seedlings were obtained. Following screening of T1 seeds with kanamycin (50 mg/l) and Claforan (166 mg/l), transformants were grown and their phenotype was observed mainly in relation to flavonoid pigmentation.

All surviving T1 seedlings (tt19/35S:AN9 line) exhibited anthocyanin pigmentation on the selection media (FIG. 7C). However, seed color at the ripening stage retained tt phenotype in all transgenic plants (FIG. 7D).

RT-PCR showed sufficient expression of AN9 in developing siliques of these T1 plants (data not shown). Control experiment with the 35S:TT19 cDNA construct confirmed the ability of TT19 to complement seed color of tt19 under the control of CaMV 35S promoter (FIG. 7D), although a few plants with pale-brown seed were included in this transgenic line (Table 1).

TABLE 1

Complementation of the tt19 phenotype in transgenic tt19 plants (T1 plants) using the wild type TT19 gene with its authentic promoter (tt19/AU:TT19 line), the 35S CaMV promoter-driven TT19 cDNA (tt19/35S:TT19 line), and the 35S CaMV promoter-driven petunia AN9 cDNA (tt19/35S:AN9 line).

| lines | No. of total | No. of seedlings with anthocyanin | No. of individuals with seed color level | | |
|---|---|---|---|---|---|
| | | | wild-type level | intermediate | tt19 level |
| tt19/AU:TT19 | 5 | 5 | 5 | 0 | 0 |
| tt19/35S:TT19 | 15 | 15 | 8 | 4 | 3 |
| tt19/35S:AN9 | 18 | 18 | 0 | 0 | 18 |

As described on the foregoing pages, the present invention provides the TT19 gene having the capability of flavonoid accumulation in the vacuoles of plant cells. Utilizing this characteristic of the TT19 gene, one may regulate its activity to control the amount of anthocyanins which are the most typical plant pigment and drawing attention as functional pigments among polyphenols, as well as controlling the amount of tannins which are also drawing attention for their antioxidizing and other actions. In particular, by activating promoters in plants so as to improve the expression of the TT19 gene, one can enhance the amount of anthocyanin accumulation in vacuoles or the amount of vacuolar accumulation of tannins. In addition, by employing the TT19 gene in bioreactors that depend on cell culture and the like, one can realize the synthesis and production of flavonoids including pigments and polyphenols.

What is claimed is:

1. A transformed plant cell containing a recombinant vector containing a nucleic acid having a nucleotide sequence selected from the group consisting of:
   (i) the nucleotide sequence represented by SEQ ID NO:1 or a nucleotide sequence which is degenerate with respect to SEQ ID NO:1;
   (ii) a nucleotide sequence which is identical to SEQ ID NO:1 except that it has deletions, substitutions or additions of one or more bases; and
   (iii) a nucleotide sequence hybridizable under stringent conditions with a nucleotide sequence complementary to the nucleotide sequence represented by SEQ ID NO:1;
   wherein the nucleotide sequence encodes a protein having at least 90% sequence identity to SEQ ID NO: 2 and having activity for vacuolar compartmentalization of proanthocyanidins in plant cells.

2. A transgenic plant containing a nucleic acid having a nucleotide sequence selected from the group consisting of:
   (i) the nucleotide sequence represented by SEQ ID NO:1 or a nucleotide sequence which is degenerate with respect to SEQ ID NO:1;
   (ii) a nucleotide sequence which is identical to SEQ ID NO:1 except that it has deletions, substitutions or additions of one or more bases; and
   (iii) a nucleotide sequence hybridizable under stringent conditions with a nucleotide sequence complementary to the nucleotide sequence represented by SEQ ID NO:1;
   wherein the nucleotide sequence encodes a protein having at least 90% sequence identity to SEQ ID NO: 2 and having activity for vacuolar compartmentalization of proanthocyanidins in plant cells.

3. A process for producing proanthocyanidins which comprises the steps of cultivating the transformed plant cell of claim 1 in a culture medium and harvesting a vacuolarly accumulated proanthocyanidin from the cultured transformed plant cell or the grown transgenic plant.

4. A transformed plant cell containing a recombinant vector containing a nucleic acid encoding a protein having an amino acid sequence selected from the group consisting of:
   (a) the amino acid sequence represented by SEQ ID NO:2; and
   (b) an amino acid sequence which is identical to SEQ ID NO:2 except that it has deletions, substitutions or additions of one or more amino acids;
   wherein the protein has at least 90% sequence identity to SEQ ID NO: 2 and has activity for vacuolar compartmentalization of proanthocyanidins in plant cells.

5. A transgenic plant containing a nucleic acid encoding a protein having an amino acid sequence selected from the group consisting of:
   (a) the amino acid sequence represented by SEQ ID NO:2; and
   (b) an amino acid sequence which is identical to SEQ ID NO:2 except that it has deletions, substitutions or additions of one or more amino acids;
   wherein the protein has at least 90% sequence identity to SEQ ID NO: 2 and has activity for vacuolar compartmentalization of proanthocyanidins in plant cells.

6. A process for producing proanthocyanidins which comprises the steps of cultivating the transformed plant cell of claim 4 in a culture medium and harvesting a vacuolarly accumulated proanthocyanidin from the cultured transformed plant cell or the grown transgenic plant.

7. A process for producing proanthocyanidins which comprises the steps of growing the transgenic plant of claim 2 and harvesting a vacuolarly accumulated proanthocyanidin from the cultured transformed plant cell or the grown transgenic plant.

8. A process for producing proanthocyanidins which comprises the steps of growing the transformed plant cell of claim 5 in a culture medium and harvesting a vacuolarly accumulated proanthocyanidin from the cultured transformed plant cell or the grown transgenic plant.

* * * * *